(12) United States Patent
Malkoff et al.

(10) Patent No.: US 12,016,751 B2
(45) Date of Patent: Jun. 25, 2024

(54) EAR COVERS

(71) Applicant: JACO ENTERPRISES, INC., Phoenix, AZ (US)

(72) Inventors: Scott Malkoff, Phoenix, AZ (US); Skyler Wirsig, Oak Grove, MO (US)

(73) Assignee: Earvolution, Inc., Scottsdale, AZ (US)

( * ) Notice: Subject to any disclaimer, the term of this patent is extended or adjusted under 35 U.S.C. 154(b) by 774 days.

(21) Appl. No.: 17/067,607

(22) Filed: Oct. 9, 2020

(65) Prior Publication Data
US 2021/0106467 A1    Apr. 15, 2021

Related U.S. Application Data

(60) Provisional application No. 62/913,594, filed on Oct. 10, 2019.

(51) Int. Cl.
*H04R 1/10* (2006.01)
*A61F 11/14* (2006.01)

(52) U.S. Cl.
CPC ............. *A61F 11/14* (2013.01); *H04R 1/10* (2013.01); *H04R 1/1058* (2013.01); *H04R 1/1066* (2013.01)

(58) Field of Classification Search
CPC ......... A61F 11/14; H04R 1/10; H04R 1/1058; H04R 1/1066
USPC ................................. 381/74, 335, 370–371
See application file for complete search history.

(56) References Cited

U.S. PATENT DOCUMENTS

| | | | |
|---|---|---|---|
| 4,546,215 | A | 10/1985 | Ferraro |
| 5,509,146 | A | 4/1996 | Bryerton, Sr. |
| 5,551,089 | A | 9/1996 | Whidden |
| 9,301,039 | B2 | 3/2016 | Brunner et al. |
| 10,344,963 | B1 | 7/2019 | Mobed et al. |
| 2004/0125976 | A1 | 7/2004 | Reneker |
| 2007/0274529 | A1 | 11/2007 | Nordin et al. |
| 2012/0140961 | A1 | 6/2012 | Reiss et al. |
| 2016/0381451 | A1 | 12/2016 | Pong et al. |
| 2018/0041827 | A1 | 2/2018 | Abdelmalek |
| 2019/0116411 | A1 | 4/2019 | Duckwall |

OTHER PUBLICATIONS

United States Internatinal Searching Authority; International Search Report & Written Opinion for PCTUS2020/055155; 8 pages; Jan. 1, 2021; Arlington, VA; US.
Amazon; Edz Capz (Carbon fibre Effect); 6 pages; https://www.amazon.co.uk/Edz-Kidz-Ear-Defenders-Blue/dp/B01FQXU5SM/ref-pd_sbs_75_2 . . . ; Oct. 10, 2019; US.
cadcrown.com; Customizable Headphone Design—Freelance 3D Modeling Design—Cad Crowd; 13 pages; https://www.cadcrowd.com/contest/1941-customizable-headphone-design; Oct. 10, 2019; US.
shop4megastore.com; Sudio Interchangeable Headphone Caps for Regent Bluetooth Wireless Headphones in Selva Azzurro Blue; 3 pages; https://www.shop4megastore.com/on-over-ear-headphones/sudio-interchangeable-headphone-c . . . ; Oct. 10, 2019; US.

(Continued)

*Primary Examiner* — George C Monikang
(74) *Attorney, Agent, or Firm* — Keith A. Vogt

(57) ABSTRACT

An ear covering device including a headband having opposing ends connected to ear cups. Outer shells are also included which are releasably connectable to the ear cups.

27 Claims, 19 Drawing Sheets

(56) References Cited

OTHER PUBLICATIONS

Poshmark; Frends Accessories from Alexis's closet on Poshmark; 15 pages; https://poshmark.com/listing/FRENDS-Taylor-stingray-headphone-caps-NEW-5d2586c2d4000 . . . Oct. 10, 2019; US.
Poshmark; Frends; 13 pages; https://poshmark.com/brand/Frends; Oct. 10, 2019; US.
Philips; PC Headset SHM7110/00; https://www.philips.co.in/c-p/SHM7110_00/pc-headset; Oct. 10, 2019; US.
amazon.com; Kids On-Ear Headphones, OneAudio Comfortable 85dB Volume Limiting Wired Headsets Lightweight Customizable Cartoon Painting DIY with 3.5mm Jack Christmas and Birthday Gift for Toddler/Children/Airplane; 10 pages; Oct. 10, 2019; US.
amazon.com: Over Ear Girls Headphones, DIY Color Unicorn Earphones with 85dB Volume limited and 3.5mm Jack for iPad Cellphones Computer MP3/4 Kindle, C hildren Headset for School, Birthday Gifts(Pink); https://www.amazon.com/dp/B07HSZ19DX/ref=sspa_dk_detail_1?psc=1&pd_rd_i=B07HSZ; 10 pages; Oct. 10, 2019.
Aequus; Customizable Planar Magnetic Headphones by C.J. Hughes; https://www.kickstarter.com/projects/cjhughes/aequus-customizable-planar-magnetic-headphones; 10 pages; Oct. 10, 2019, US.
Omanoff; Explore Foldable Volume Limiting Kids Headphones—Durable, Comfortable & Customizable—Built in Headphone Splitter and In Line Mic—For iPad, Fire, Computers and Tablets—Red; 2 pages; https://www.keeboshop.com/products/explore-foldable-volume-limiting- . . . ; Oct. 10, 2019; US.
amazon.com; Marble Pattern Design Skinz Premium Full-Body Cover Wrap Decal Skin-Kit for the Beats by Dre studio 3 Wireless—Marbleized Teal and Pink V2; 5 pages; 5 pages; Oct. 10, 2019; US.
amazon.com; iiRov Night Aerial NYC DesignSkinz Full-Body Skin Kit; 6 pages; US.
amazon.com; Avokado Caps—Washable headphone covers (Blue Garden, L); 7 pages; US.

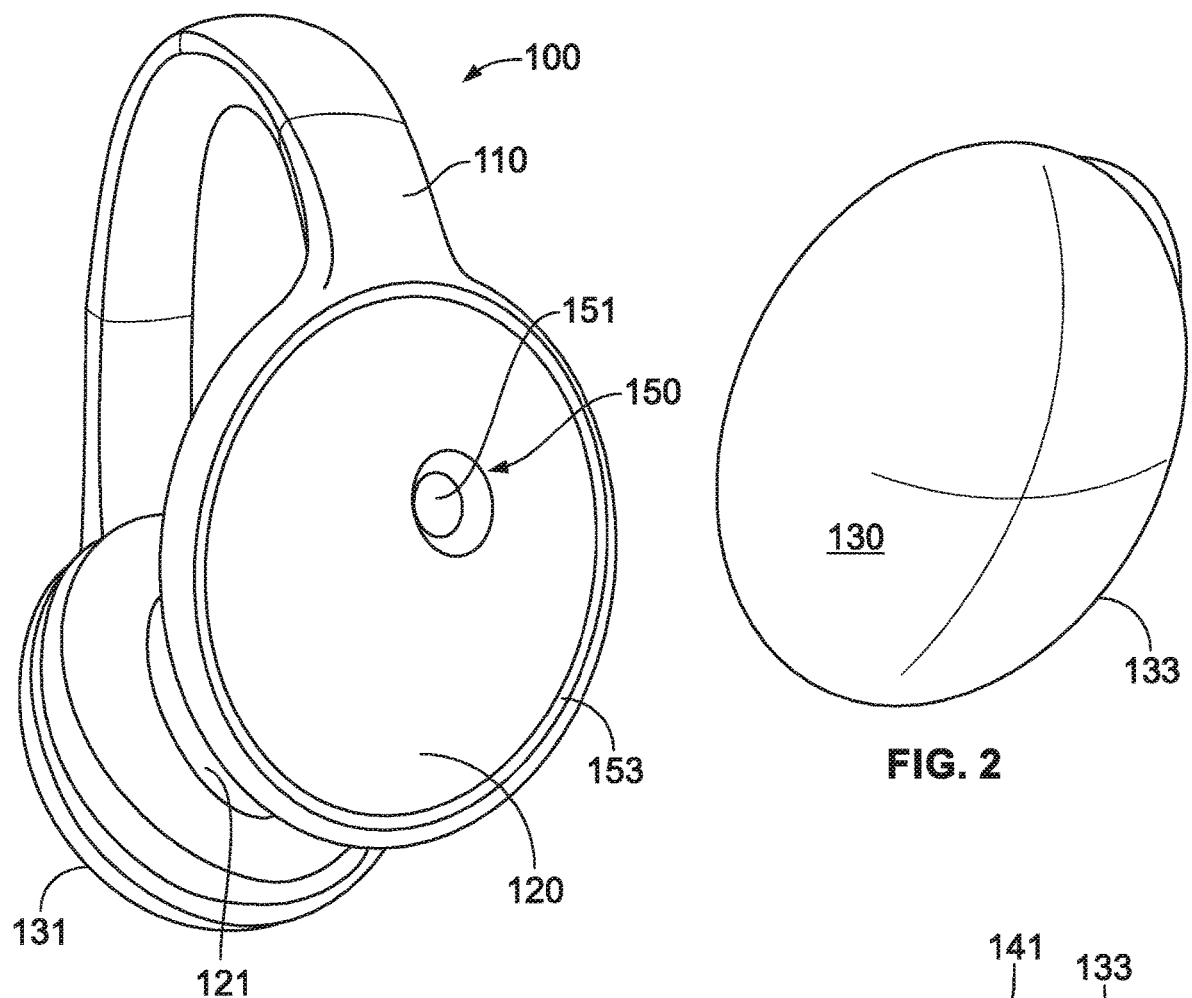
FIG. 1
FIG. 2
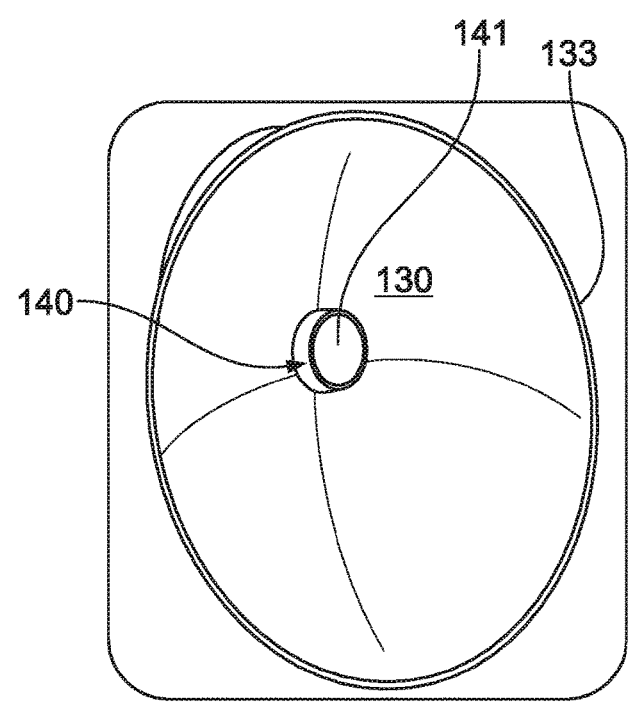
FIG. 3

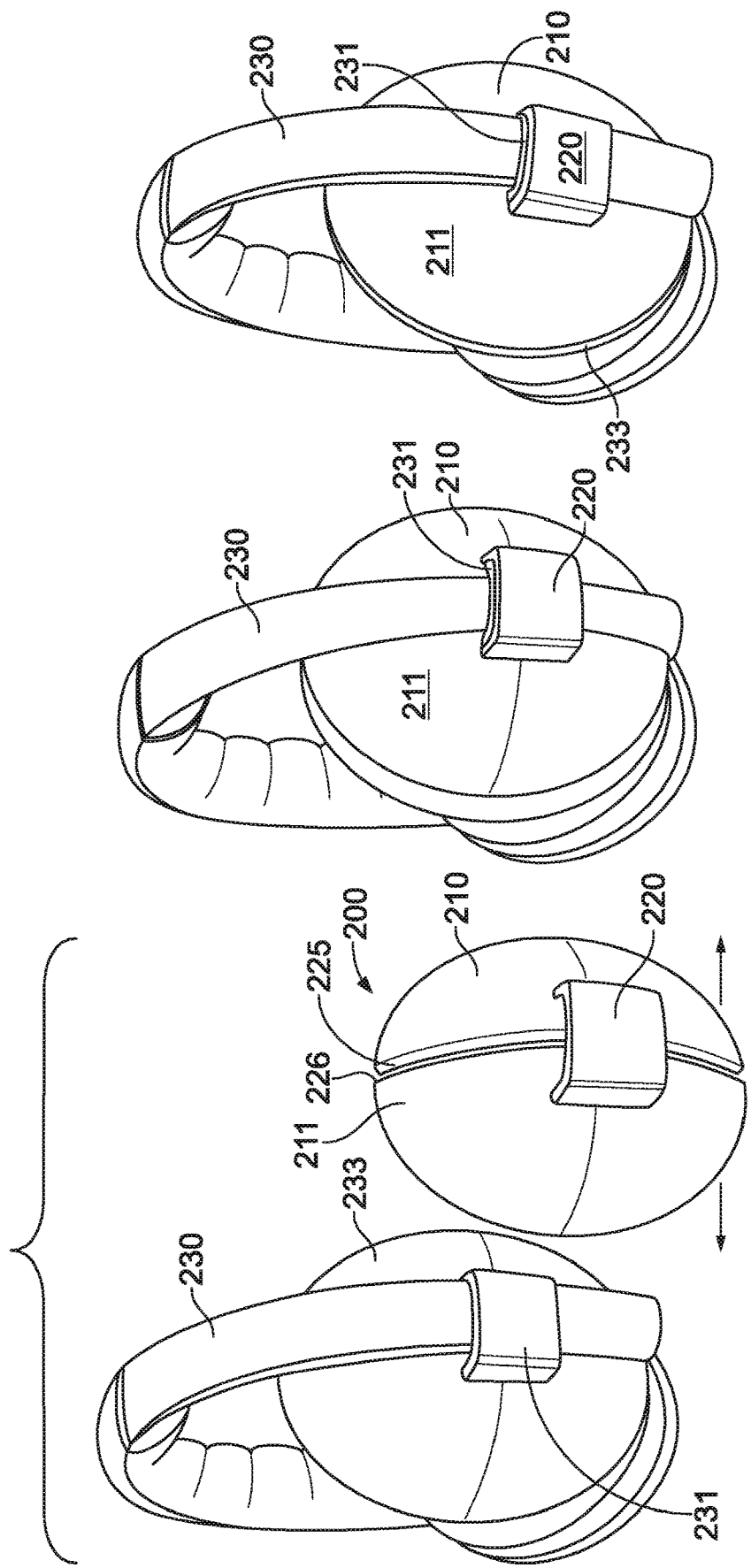

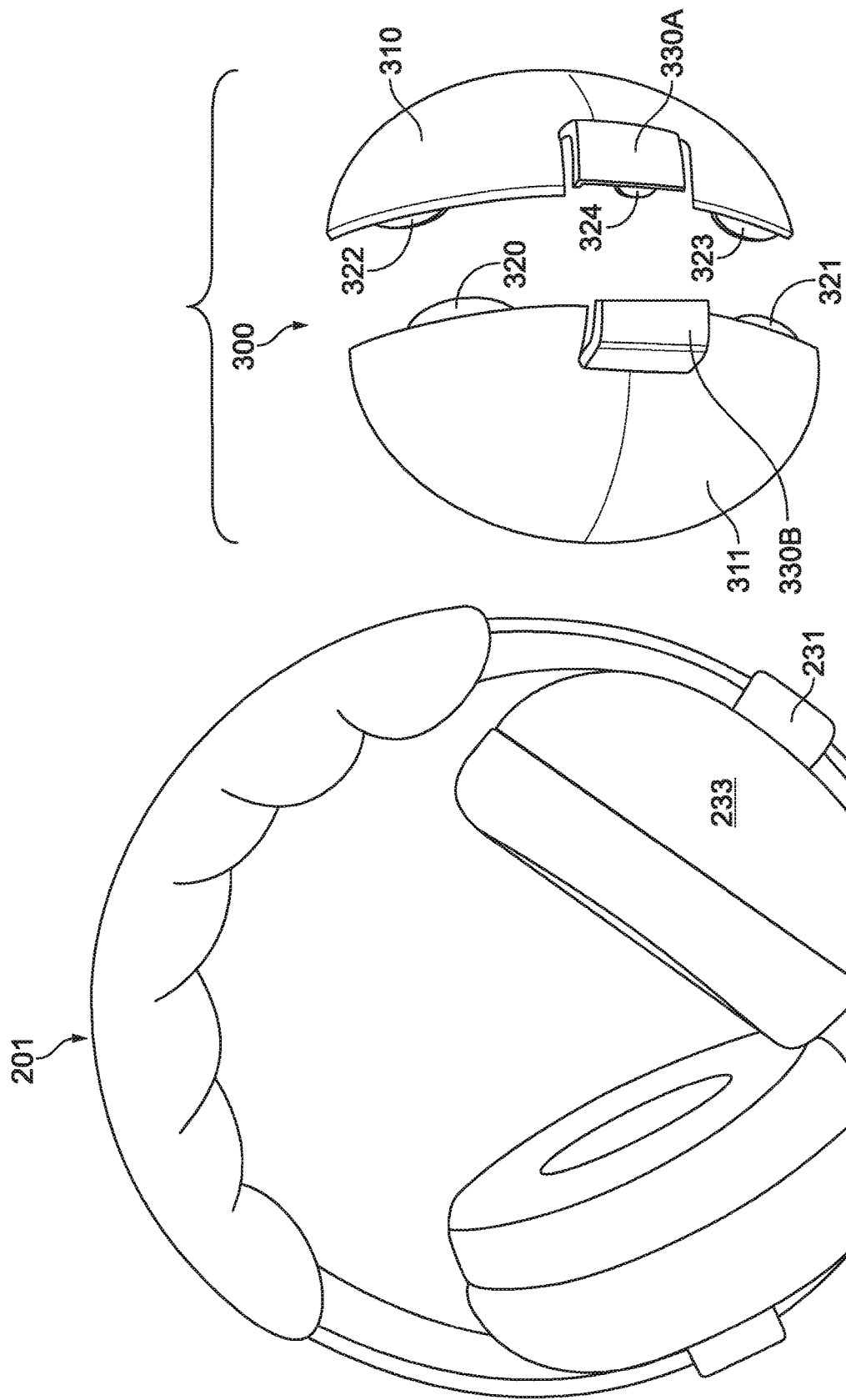

EAR COVERS

RELATED APPLICATIONS

This application claims priority to U.S. Provisional Application No. 62/913,594 filed Oct. 10, 2019, which is incorporated herein in its entirety

STATEMENT REGARDING FEDERALLY SPONSORED RESEARCH & DEVELOPMENT

Not applicable.

INCORPORATION BY REFERENCE OF MATERIAL SUBMITTED ON A COMPACT DISC

Not applicable.

BACKGROUND OF THE INVENTION

The present invention relates to the field of sound protection apparatus.

SUMMARY OF THE INVENTION

In one embodiment, the present invention concerns an ear cover comprising an outer shell that is releasably detachable to an ear cup thus allowing the appearance of the ear cover to be changed as desired by selecting an appropriate outer shell.

In another embodiment, the present invention concerns an ear cover comprising an outer shell that is releasably detachable to an ear cup by the use of a magnetic connection.

In another embodiment, the present invention concerns an ear cover including a projection and recess that magnetically mate together.

In another embodiment, the present invention concerns an ear cover comprising sections of a detachable outer shell that snap-fit together to cover an ear cup.

In another embodiment, the present invention concerns an ear cover wherein sections of a detachable outer shell define a slot, and the slot is adapted to fit over a slot on an ear cup that has a headband passing through.

In another embodiment, the present invention concerns an ear cover comprising an ear cup adapted to form a snap-fit with an outer shell to form a releasable connection between the outer shell and ear cup.

In another embodiment, the present invention concerns an ear cover wherein a two-piece snap forms the releasable connection between the outer shell and ear cup.

In another embodiment, the present invention concerns an ear cover further including a telescoping headband section which makes the headband adjustable to fit various users.

In another embodiment, the present invention concerns removable shells using magnets.

In another embodiment, the present invention concerns an ear cover having a telescoping headband and ear cups.

In another embodiment, the present invention concerns an ear cover having a headband comprised of three total pieces including a middle part that acts as a housing with the inside formed with shutoffs.

In another embodiment, the present invention concerns an ear cover having maximized adjustability by providing stopping mechanisms.

In another embodiment, the present invention concerns an ear cover using a single screw to attach the ear cup to the headband thereby allowing for ease of manufacturing and less small parts, increasing the safety of the invention.

In another embodiment, the present invention concerns an ear cover that maximizes adjustability thereby allowing the device to be used with infant and children's head sizes creating optimal comfort and seal.

In another embodiment, the present invention concerns an ear cover having a multi-piece telescoping headband. The headband sections meet at the top of the head at the smallest setting and pull apart at the largest setting with ridges to allow for multiple settings to fit a wide range of head sizes.

In another embodiment, the present invention concerns an ear cover having a dedicated curved channel/slot at the top of the main ear cup piece to attach the headband.

In another embodiment, the present invention concerns an ear cover having a channel formed by inner ear padding frame/outer ear cup designed to allow the band to attach inside the two with one screw holding the band instead of two, for ease of manufacturing, safety, and better noise attenuation by eliminating any gaps where sound could penetrate through the ear cup and into the ear padding frame.

In another embodiment, the present invention concerns an ear cover having a snap-fit between the outer ear cup to improve noise attenuation. In yet another embodiment, the present invention concerns an ear cover having a snap-fit between the outer ear cup and inner ear padding frame that allows for a better seal than screws alone and, thus, increased noise attenuation.

In another embodiment, the present invention concerns an ear cover with headbands having a shoulder at their ends to help keep the band from moving from side to side. This also allows for the visible, wider portion of the headband to line up to the channeled slot without flare, improving the invention's appearance.

In another embodiment, the present invention concerns an ear cover having earmuffs to optimize fit/seal and to attenuate noise. The headband has a uniform curve to it but then at each end the angle changes. Each end slants inward towards the users' ears, thus, allowing the earmuff to rest more securely to a user while maximizing the seal to improve noise reduction.

In another embodiment, the present invention concerns an ear cover having oversized ear cups which are larger and deeper than standard designs to allow for more foam to fit inside than current earmuffs, thereby improving attenuation.

In another embodiment, the present invention concerns an ear cover having a plastic ear padding frame wherein the ear padding connects to and around which is a snap-fit design. The snap-fit seals off sound and is also easier to assemble. The footprint of this piece of ear padding frame is a little larger than the main ear cup and allows for the outer shell to fit snugly against it, completing a clean look and uniform shape.

In another embodiment, the present invention concerns an ear cover having a built-in magnet cylinder-shaped slot inside of the inner earcup. The magnet is secured with a plastic cover and screw on the inside and the slot has a hole that is narrower than the magnet which positively retains the magnet to prevent its removal from outside of the ear cup. This prevents the magnet from coming out or being pulled out, which is important for safety.

In another embodiment, the present invention concerns an ear cover having a steel pin secured in an outer shell by tapering the pin and molding it into the plastic shell, so that it cannot fall or be pulled out, which is important for child safety.

In another embodiment, the present invention concerns an ear cover having an N52 Magnet with ¼" thickness, which optimizes the strength to secure the shell in place, while not requiring too much effort to remove. However, the force is strong enough to assist in preventing small children from removing the shell.

In another embodiment, the present invention concerns an ear cover having a lightweight, simplified shell design that provides a low cost means to create multiple looks (colors, patterns, licensing) and make the earmuff more of a fashion/style product at a reasonable cost.

In another embodiment, the present invention concerns an ear cover having outer shells that mirrors a channeled headband slot and covers that portion. This not only is aesthetically pleasing but it also helps to keep the outer shells in place with the unique shape at the top. The shell cannot be twisted off or easily taken off because of this and must be pulled perfectly outward/away from the ear cup to be removed.

It is to be understood that both the foregoing general description and the following detailed description are exemplary and explanatory only and are not restrictive of the invention, as claimed.

BRIEF DESCRIPTION OF THE SEVERAL VIEWS OF THE DRAWINGS

In the drawings, which are not necessarily drawn to scale, like numerals may describe substantially similar components throughout the several views. Like numerals having different letter suffixes may represent different instances of substantially similar components. The drawings illustrate generally, by way of example, but not by way of limitation, a detailed description of certain embodiments discussed in the present document.

FIG. 1 illustrates a first embodiment of the present invention.

FIG. 2 illustrates the exterior of an outer shell that may be used with the embodiment shown in FIG. 1.

FIG. 3 illustrates the underside of the outer shell shown in FIG. 3.

FIG. 12 illustrates how the outer shell shown in FIG. 11 may be manipulated for attachment to an ear cup.

FIG. 13 illustrates how the outer shell shown in FIG. 11 may be further manipulated for attachment to an ear cup.

FIG. 14 illustrates how the outer shell shown in FIG. 11 may be attached to an ear cup.

FIG. 15 shows a prior art ear cover.

FIG. 16 illustrates an outer shell for use with a fourth embodiment of the present invention.

DETAILED DESCRIPTION OF THE INVENTION

Figure 5:
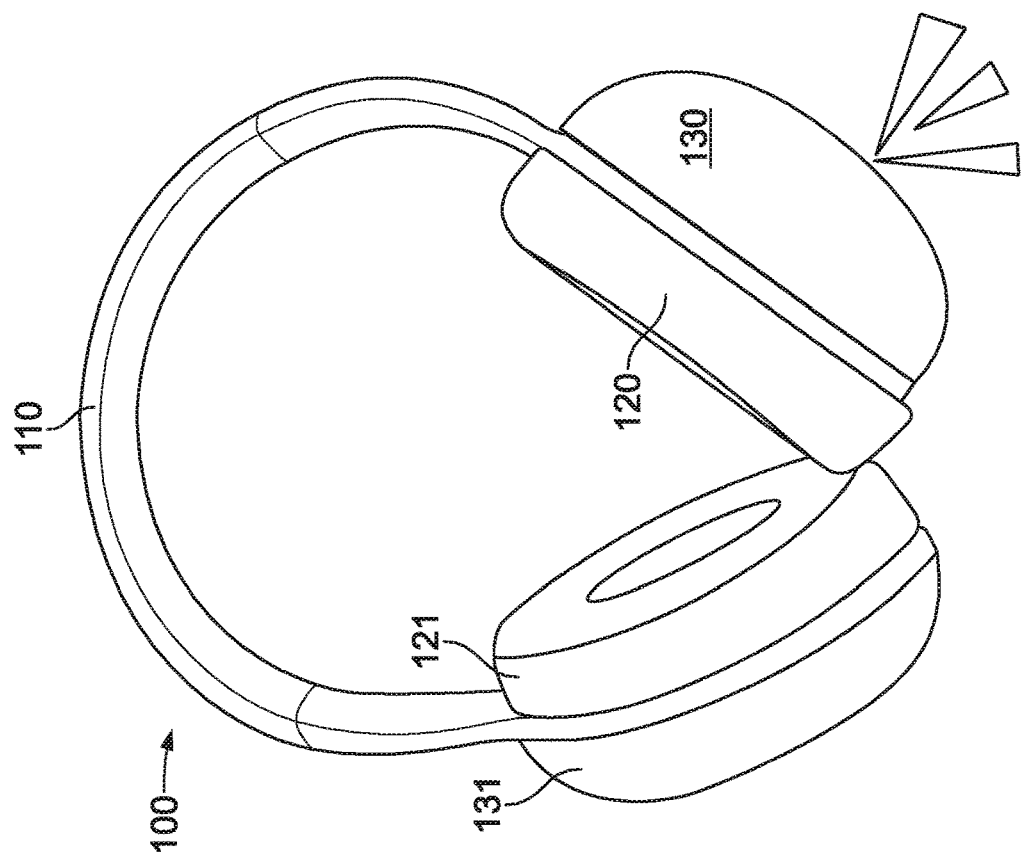
FIG. 5 illustrates how outer shells may be attached for the first embodiment of the present invention.

Detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a representative basis for teaching one skilled in the art to variously employ the present invention in virtually any appropriately detailed method, structure or system. Further, the terms and phrases used herein are not intended to be limiting, but rather to provide an understandable description of the invention.

As shown in FIGS. 1-5, a first embodiment of the present invention concerns cover 100 which is comprised of headband 110 and ear cups 120 and 121. As is also shown, each ear cup is adapted to receive outer shells 130 and 131. Outer shells 130 and 131 may be printed with graphics and images on their outer surfaces and may be made in a variety of shapes and colors. The outer shells are releasably detachable to ear cups 120 and 121 thus allowing the appearance of cover 100 to be changed as desired by selecting an appropriate outer shell.

As shown in FIGS. 1 and 3, shells 130 and 131 may be releasably detachable to ear cups 120 and 121 by the use of a magnetic connection. In a preferred embodiment, each shell such as outer shell 130 has a boss or projection 140 having a first material 141. Projection 140 is designed to fit into recess 150 which includes therein a second material 151. Projection 140 may be tapered or form as a truncated cone and recess 150 mimics the shape of projection 140 to form a mating or nesting relationship between projection 140 and recess 150. First material 141 and second material 151 are magnetically attracted to each other. Thus one of the materials may be a magnet and the other metallic or both may be magnetic.

In another embodiment, outer shells 130 and 131 have edges that fit into an annular rim on the ear cups. As shown in FIGS. 1 and 3, shell 130 has edge 133 adapted to fit within annular rim 153 on ear cover 120. As is also shown, the footprint or upper section of rim 153 is a little larger than edge 133 of shell 130 to create a snug fit and a clean look, and uniform shape.

Figure 4:
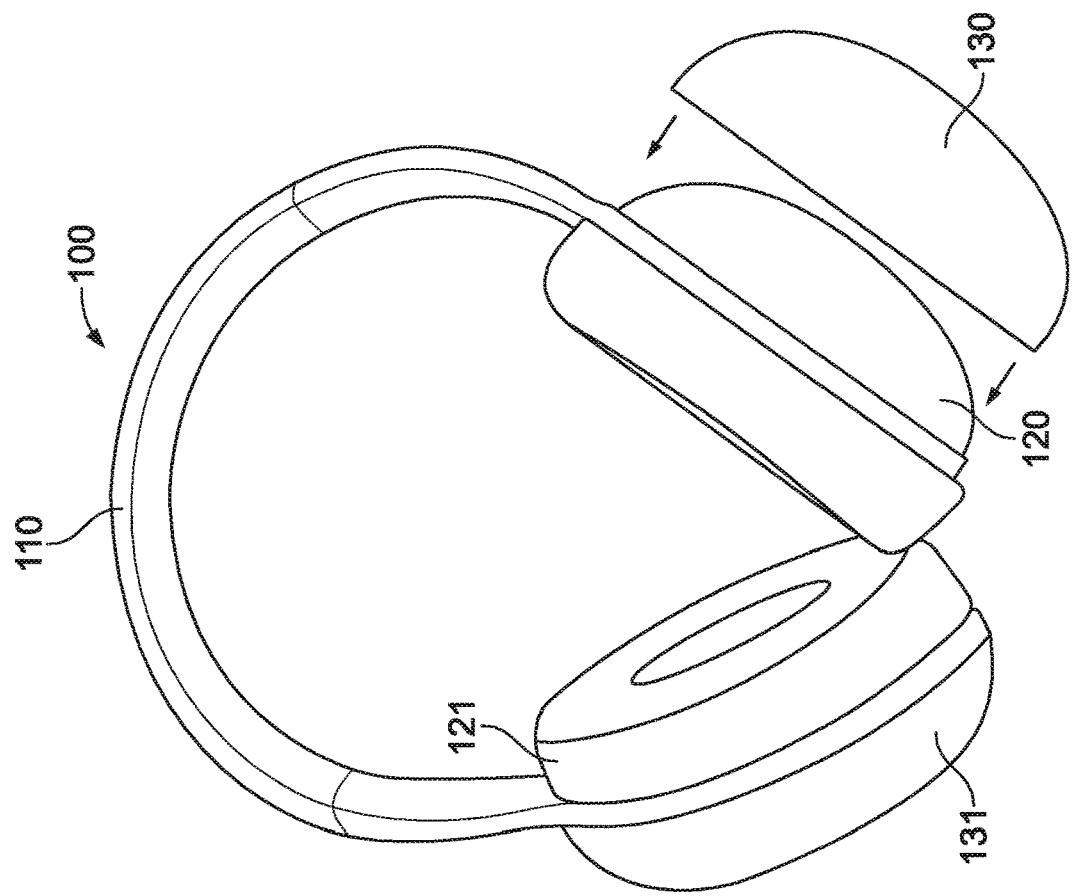
FIG. 4 illustrates how outer shells may be attached for the first embodiment of the present invention.
Figure 6:
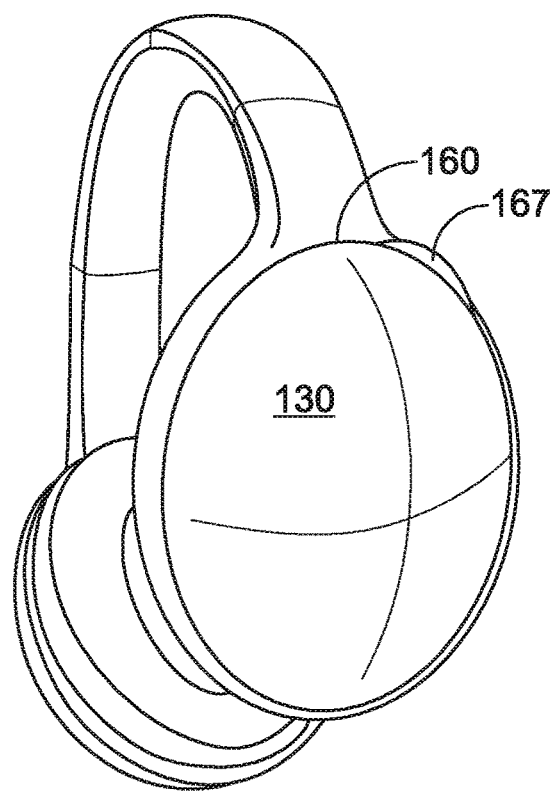
FIG. 6 illustrates a second embodiment of the present invention.
Figure 7:
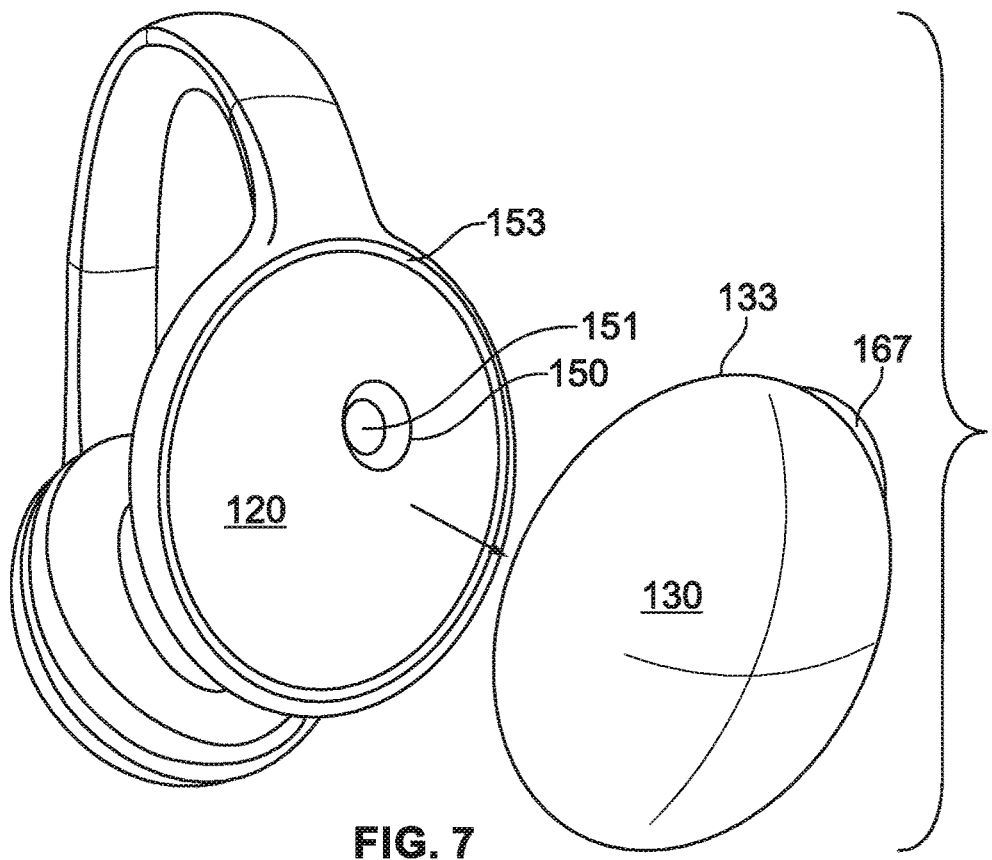
FIG. 7 illustrates how outer shells may be magnetically attached for a second embodiment of the present invention.
Figure 8:
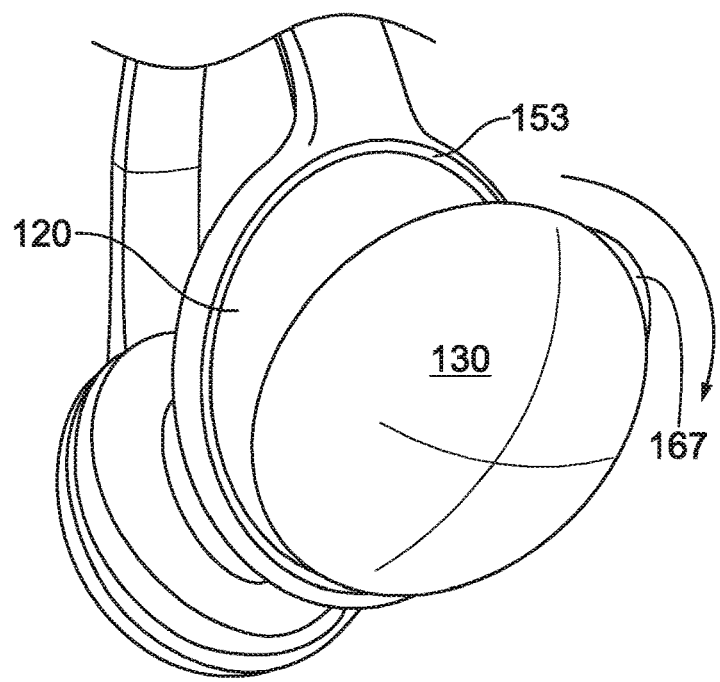
FIG. 8 illustrates how outer shells may be magnetically removed for a second embodiment of the present invention.

As shown in FIGS. 4 and 5, using a magnetic connection creates an audible click when the outer shells come into contact and are attached to the ear cups. As is also shown in FIGS. 6-8, for a second embodiment of the present invention, removing the magnetically connected shells may also be accomplished by a twist and pull motion. Tab 167 may be included on shell 130, as well as shell 131, to facilitate this operation.

Figure 9:
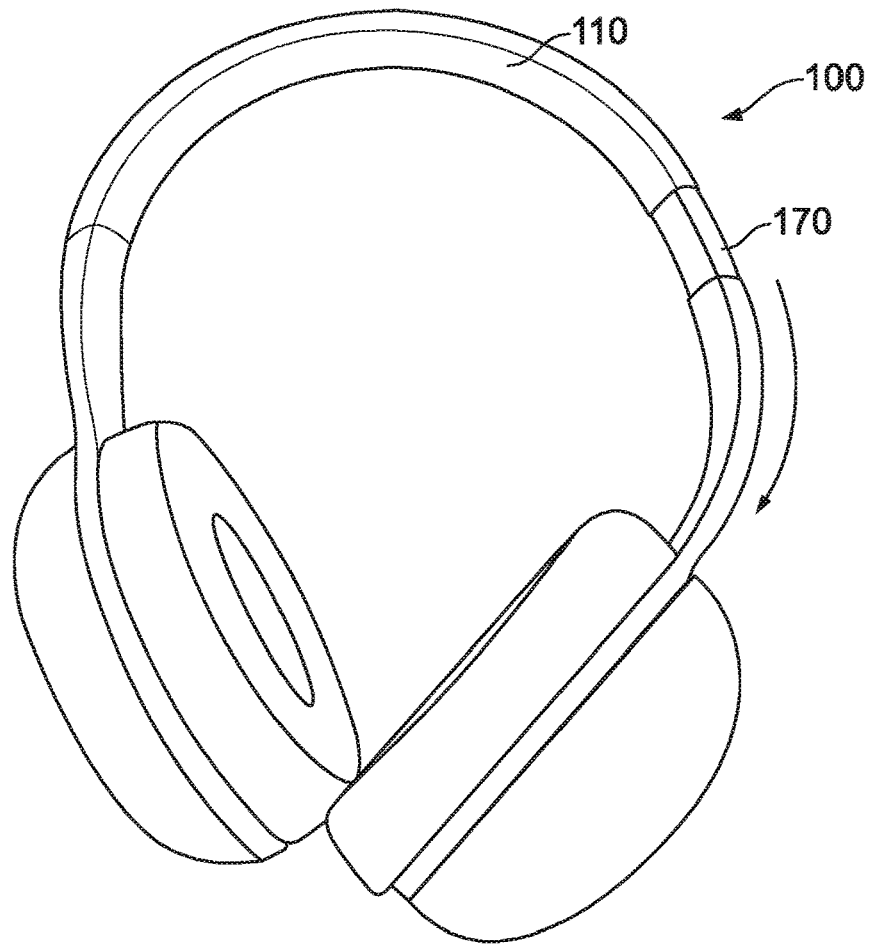
FIG. 9 illustrates a telescoping headband for use with the embodiments of the present invention.
Figure 11:
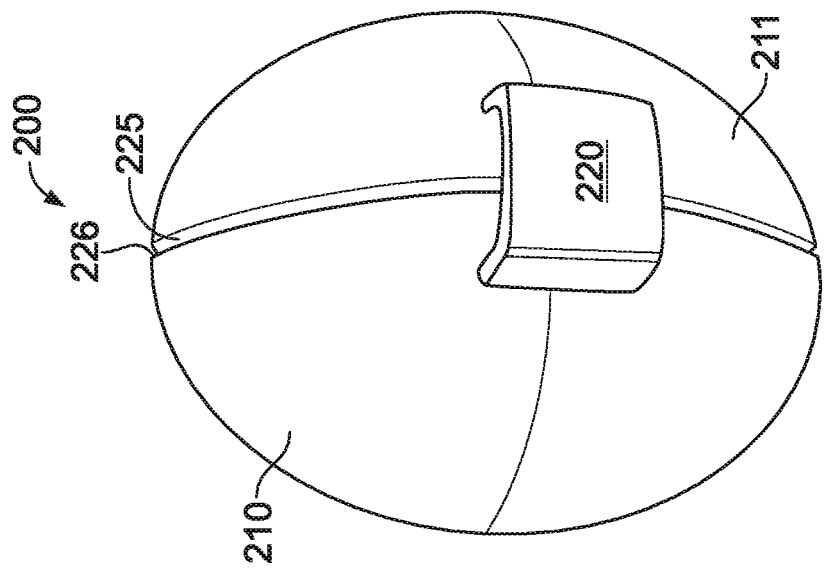
FIG. 11 illustrates an outer shell for use with a third embodiment of the present invention.

FIG. 9 shows another embodiment of the present invention. For this embodiment, headband 110 includes telescoping section 170 which makes the headband adjustable to fit various users.

Figure 10:
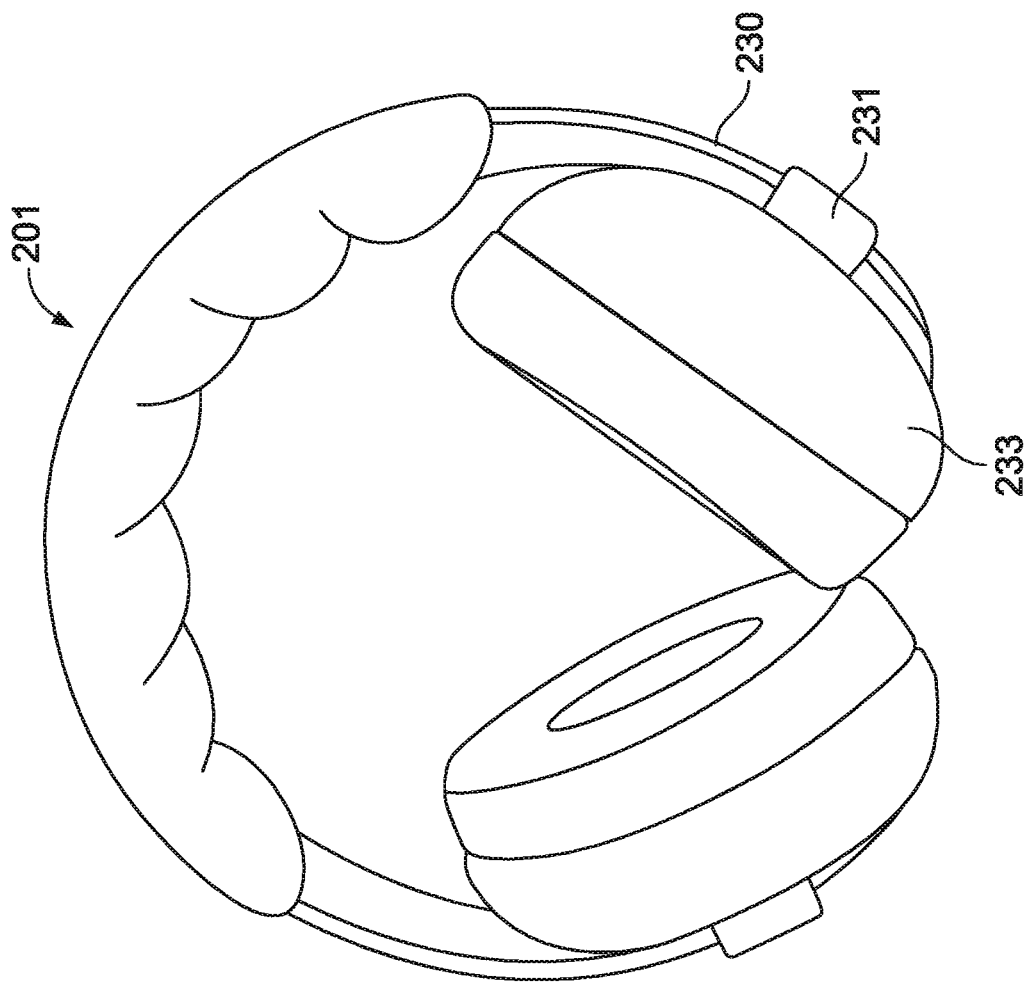
FIG. 10 shows a prior art ear cover.

FIGS. 11-14 illustrate a third embodiment of the present invention adapted to work with prior art device 201 which is shown in FIG. 10. This embodiment provides outer shells, such as shell 200. As is further shown in FIGS. 11-14, outer shell 200 is comprised of halves or sections 210 and 211 connected by a common flexible center channel 220. Channel 220 is designed to form a snap-fit over boss 231 found on arm 230 of the prior art device 201. In operation, shell 200 is designed to fit over an existing ear cover 233 by pulling or splaying sections 210 and 211 outwardly into an open position so that edges 225 and 226 move away from each other as shown in FIG. 12. This allows channel 220 to be fitted over boss 231 as shown in FIG. 13. Once channel 220 is placed over boss 231, flexible channel 220 returns to its closed position when edges 225 and 226 are urged towards one another into a closed position. Channel 220 affixes to boss 231 making shell 200 releasably attached to ear cover 233.

Figure 18:
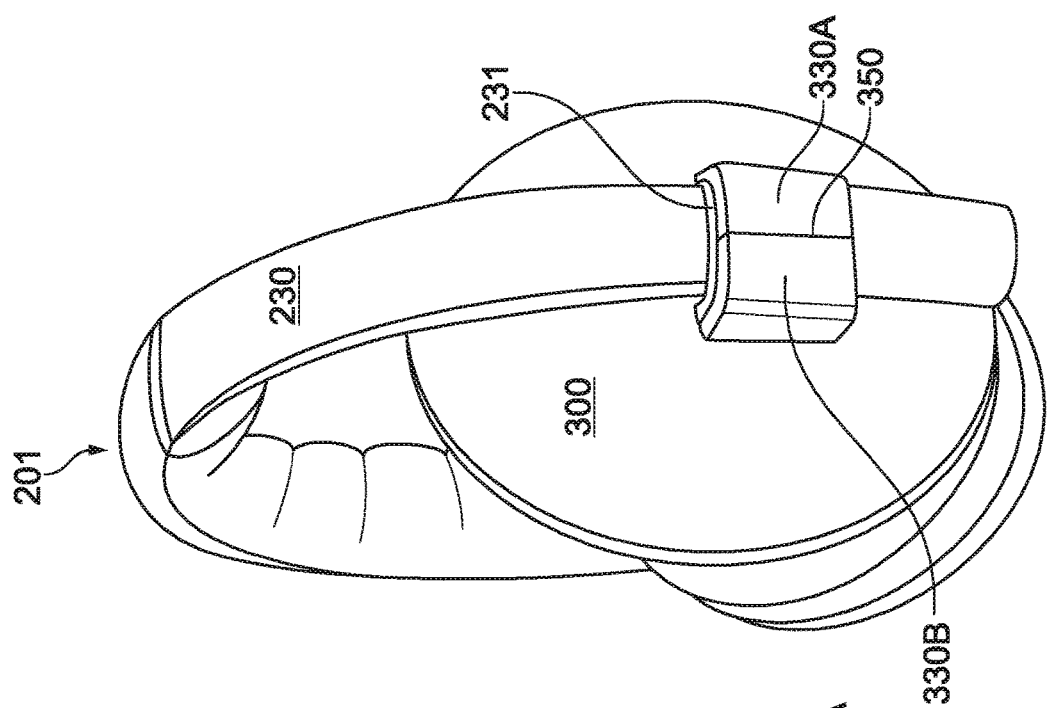
FIG. 18 illustrates how the outer shell shown in FIG. 16 may be attached to an ear cup.
Figure 17:
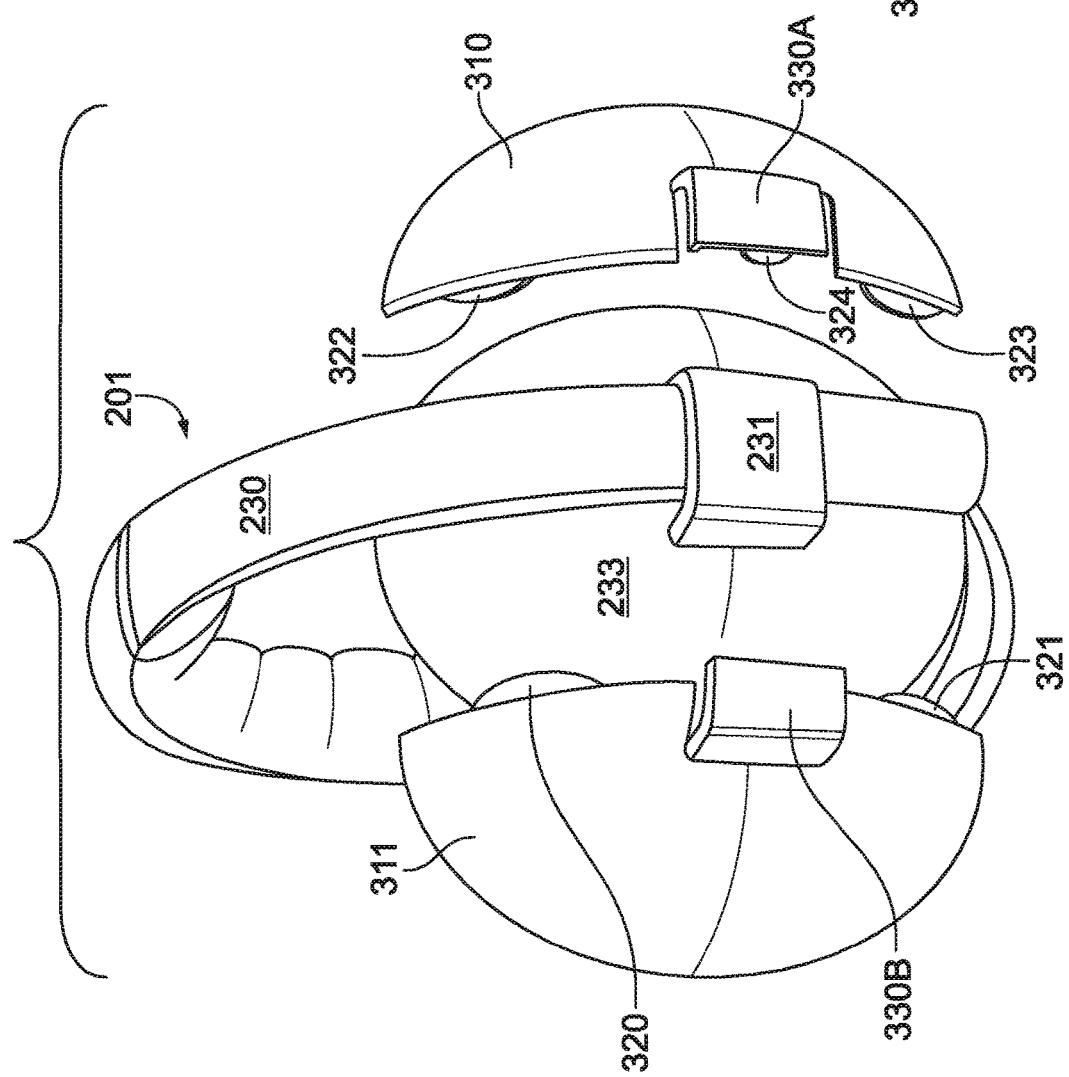
FIG. 17 illustrates how the outer shell shown in FIG. 16 may be manipulated for attachment to an ear cup.
Figures 19, 20:
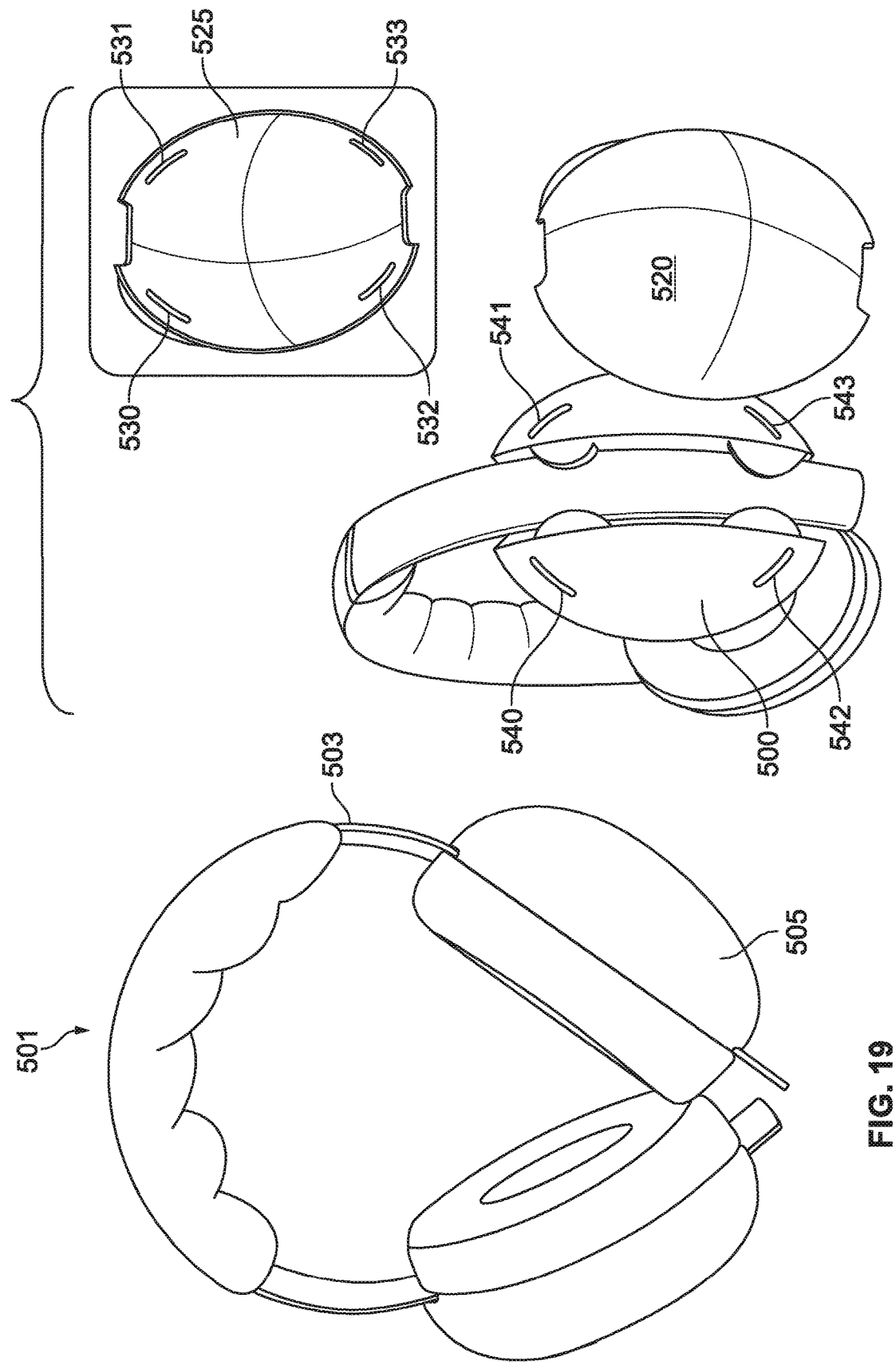
FIG. 19 shows a prior art ear cover.
FIG. 20 illustrates an outer shell for use with a fifth embodiment of the present invention.
Figure 22:
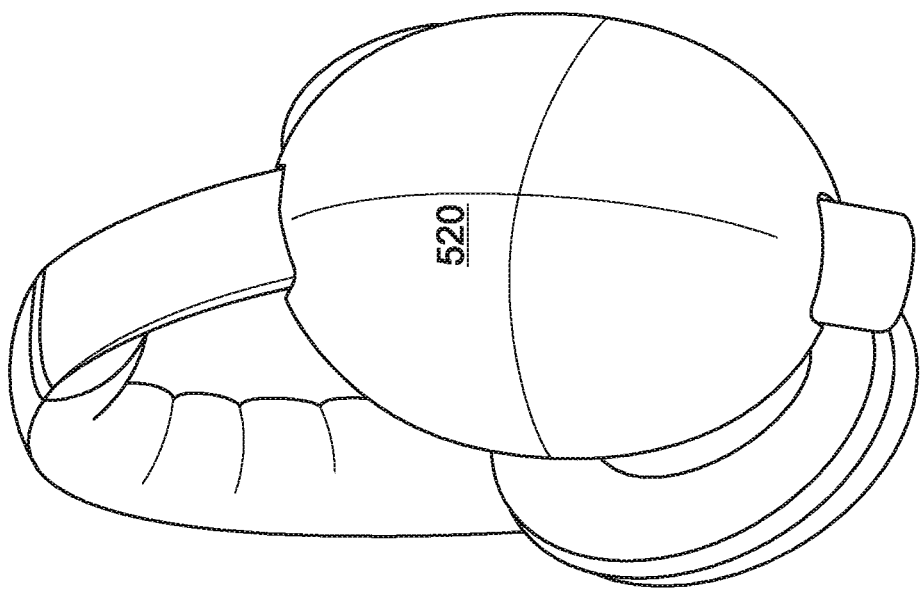
FIG. 22 illustrates how the outer shell shown in FIG. 20 may be attached to an ear cup.
Figure 21:
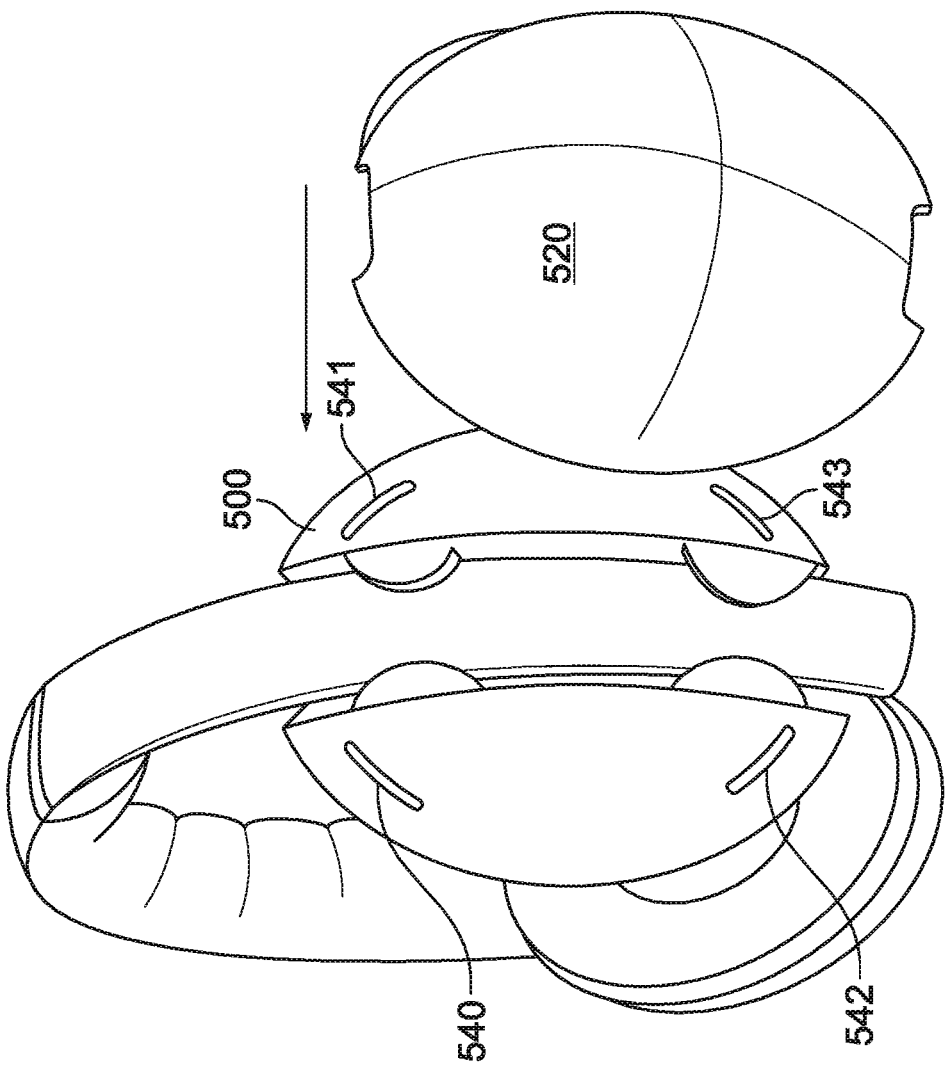
FIG. 21 illustrates how the outer shell shown in FIG. 20 may be manipulated for attachment to an ear cup.
Figure 24:
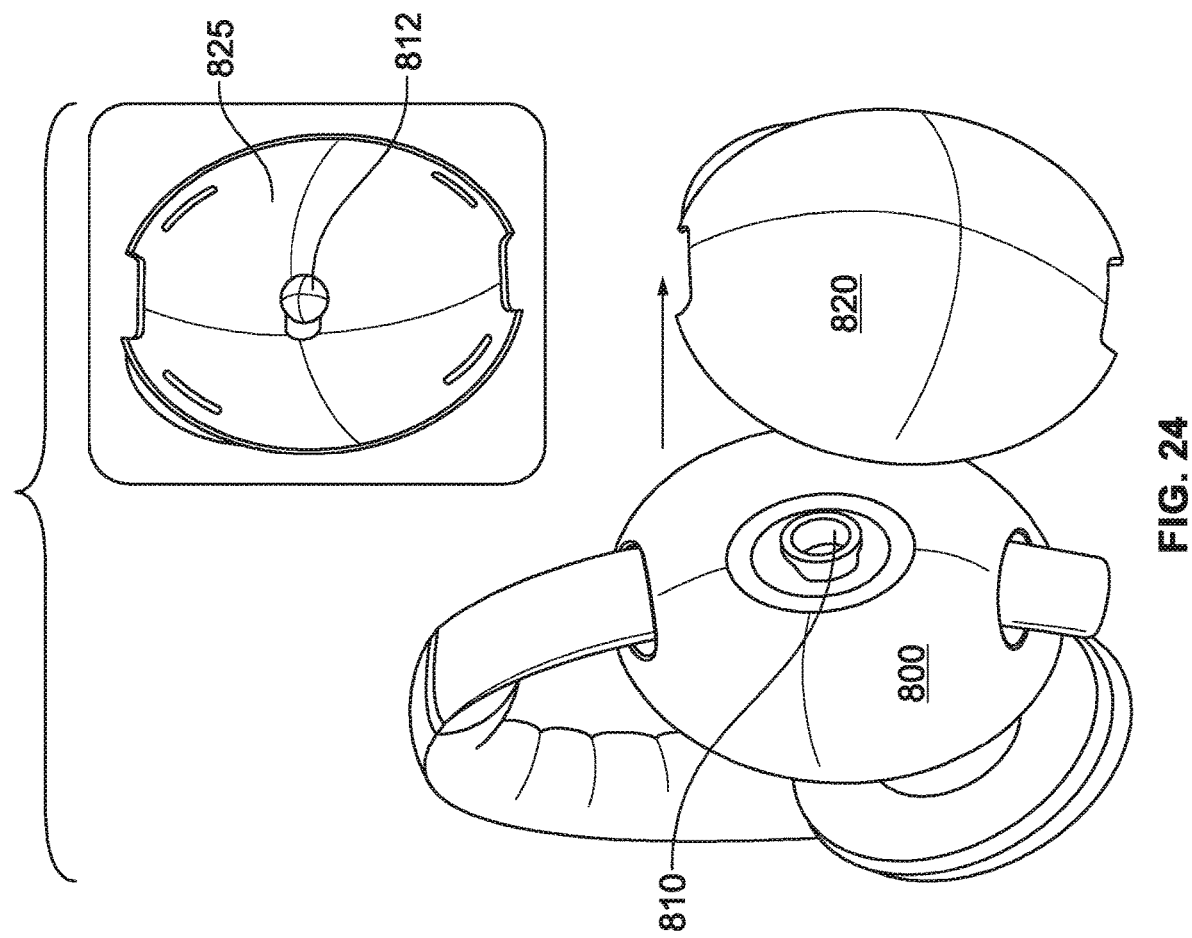
FIG. 24 illustrates an outer shell for use with a sixth embodiment of the present invention.
Figure 23:
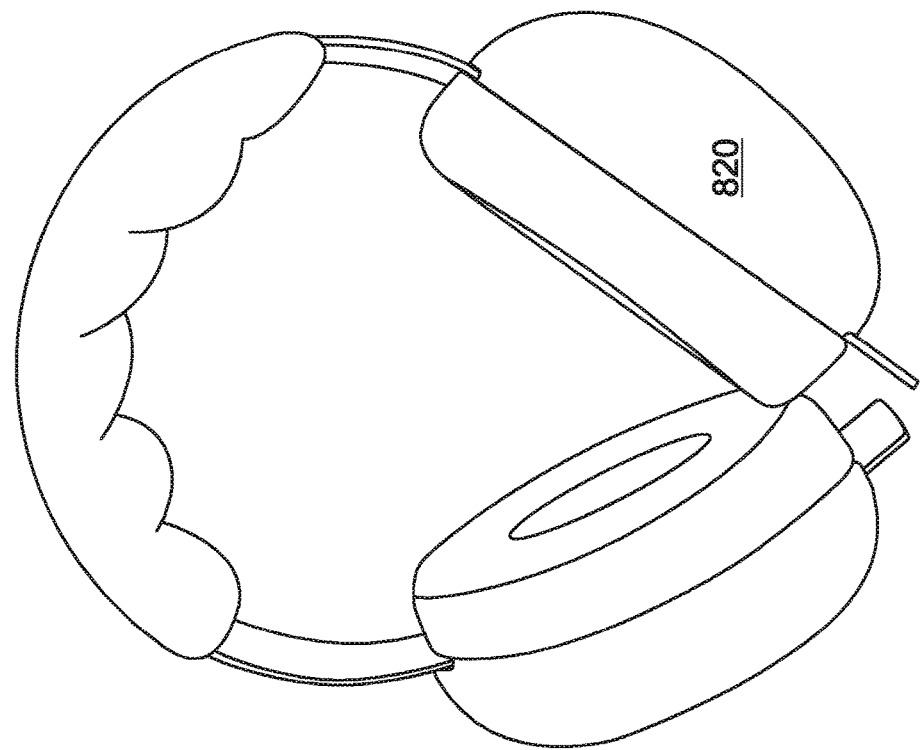
FIG. 23 shows a prior art ear cover.
Figure 26:
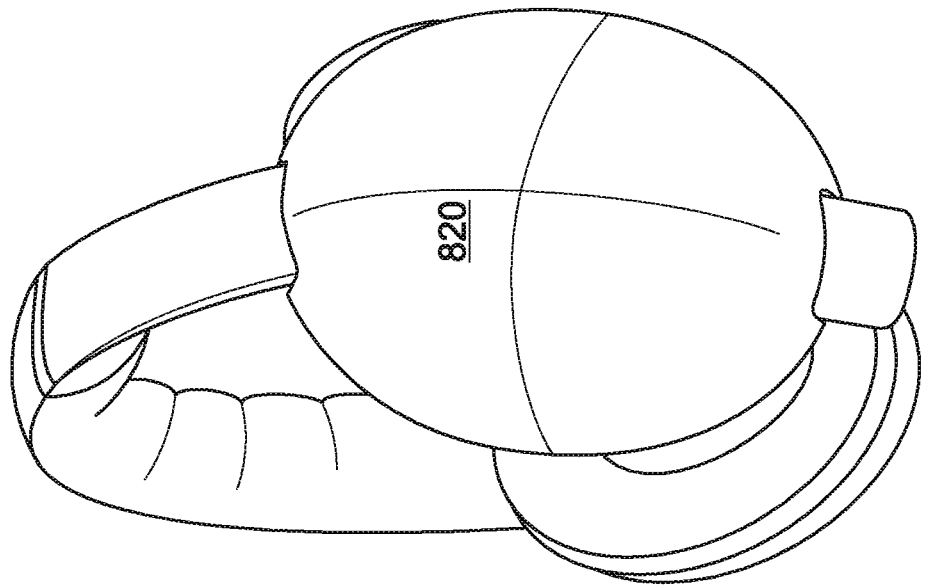
FIG. 26 illustrates how the outer shell shown in FIG. 24 may be attached to an ear cup.
Figure 25:
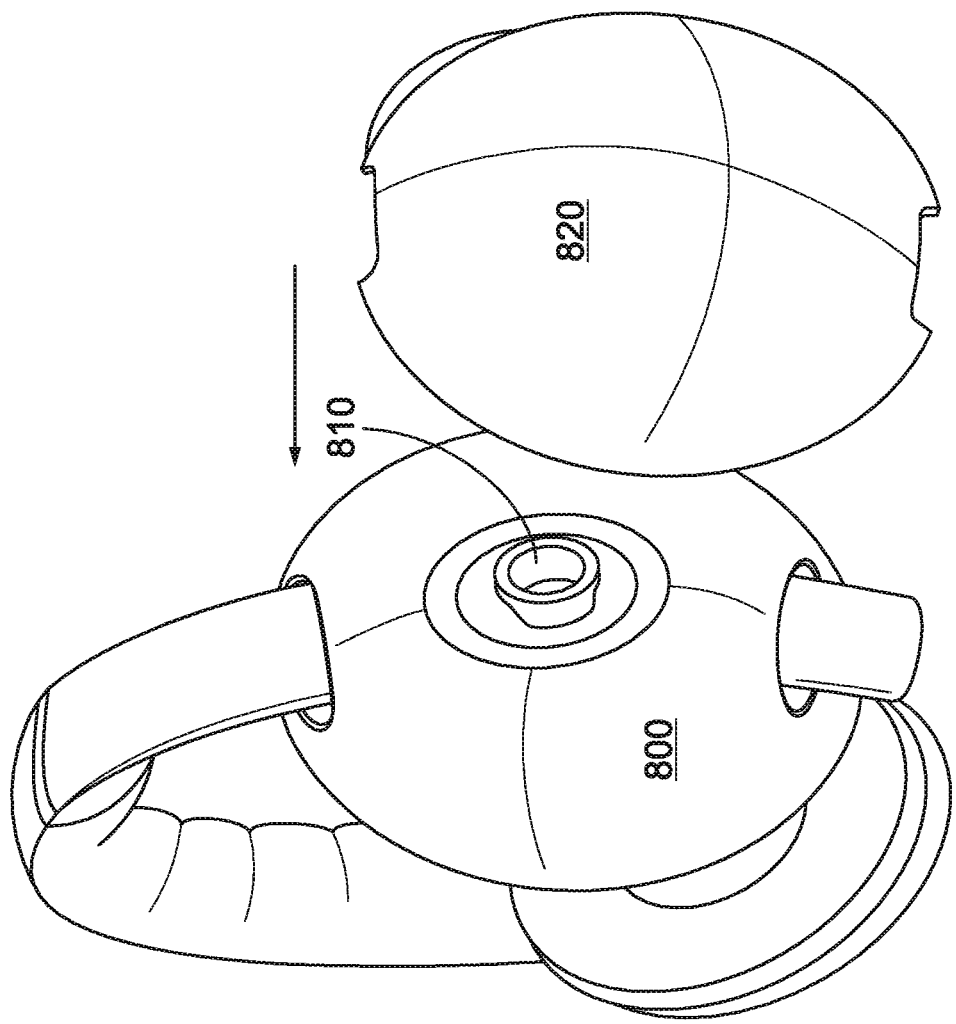
FIG. 25 illustrates how the outer shell shown in FIG. 24 may be manipulated for attachment to an ear cup.

FIGS. 15-18 illustrate a fourth embodiment of the present invention adapted to work with prior art device 201. This embodiment provides outer shells, such as shell 300. As is further shown, shell 300 is comprised of halves or sections 310 and 311, which may be mirror images, and which are connected by tabs 320-324. Channel 350 is formed when sections 330A and 330B are connected. Channel 350 is designed to fit over boss 231 found on arm 230 of the prior art device 201. In operation, shell 300 is designed to fit over an existing ear cover 233 by connecting sections 310 and 311 together as shown in FIGS. 17-18. This allows channel 350 to be fitted over boss 231 as shown.

FIGS. 19-22 illustrate a fifth embodiment of the present invention. For this embodiment, pad 500 is adapted to form a snap-fit with outer shell 520 to form cover 501 having headband 503 and cover 505. A releasable connection pad 500 and shell 520 is created by tabs 530-533 on underside 525 of shell 520. The tabs are positioned to engage slots 540-543 in pad 500 to form a friction fit.

FIGS. 23-26 illustrate a sixth embodiment of the present invention. As shown, ear cup 800 includes snap 810 that is adapted to releasably engage snap 812 on the underside 825 of outer shell 820. This forms a releasable connection between the outer shells and ear cups.

Figure 27:
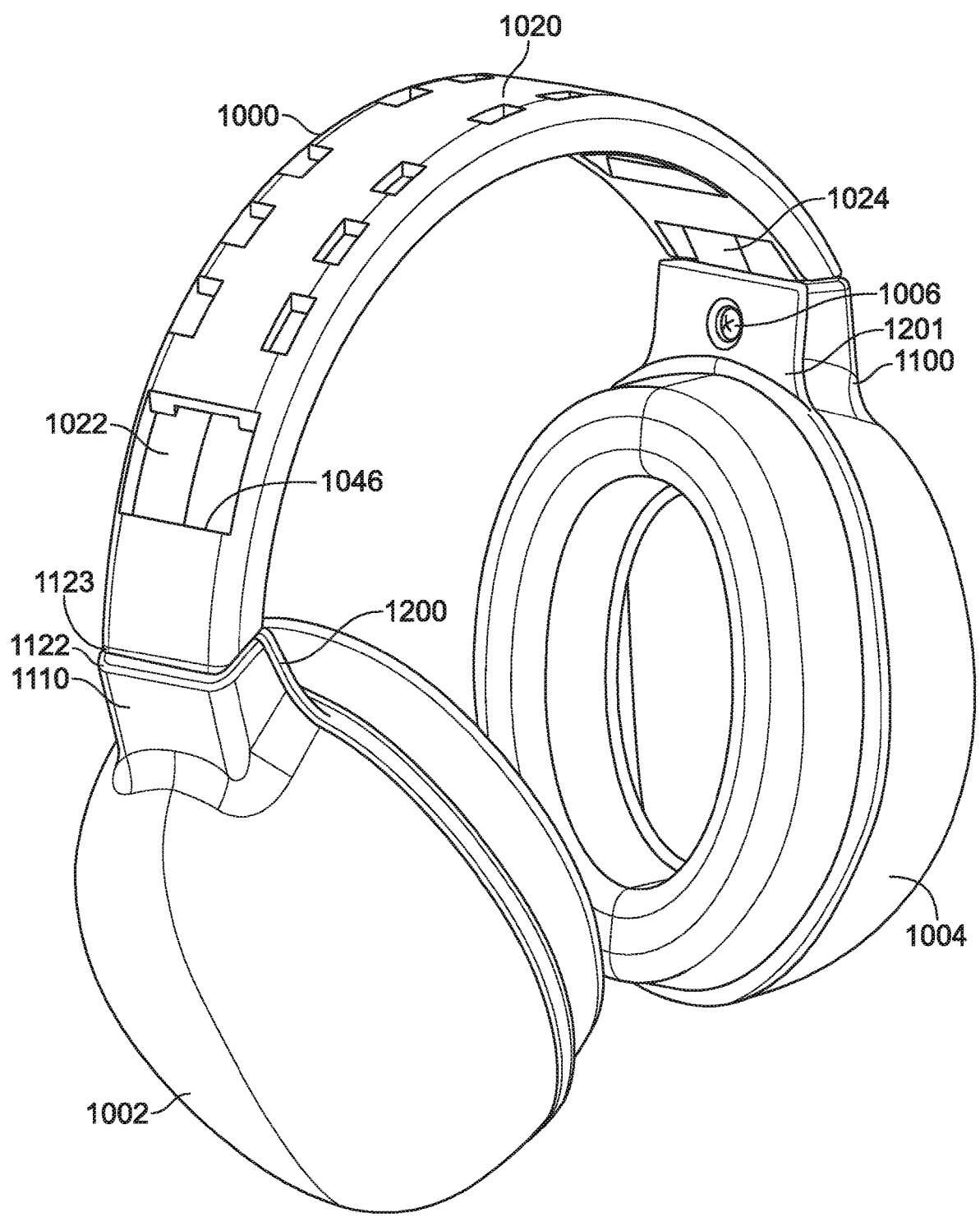
FIG. 27 is a perspective view of a seventh embodiment of the present invention.
Figure 28:
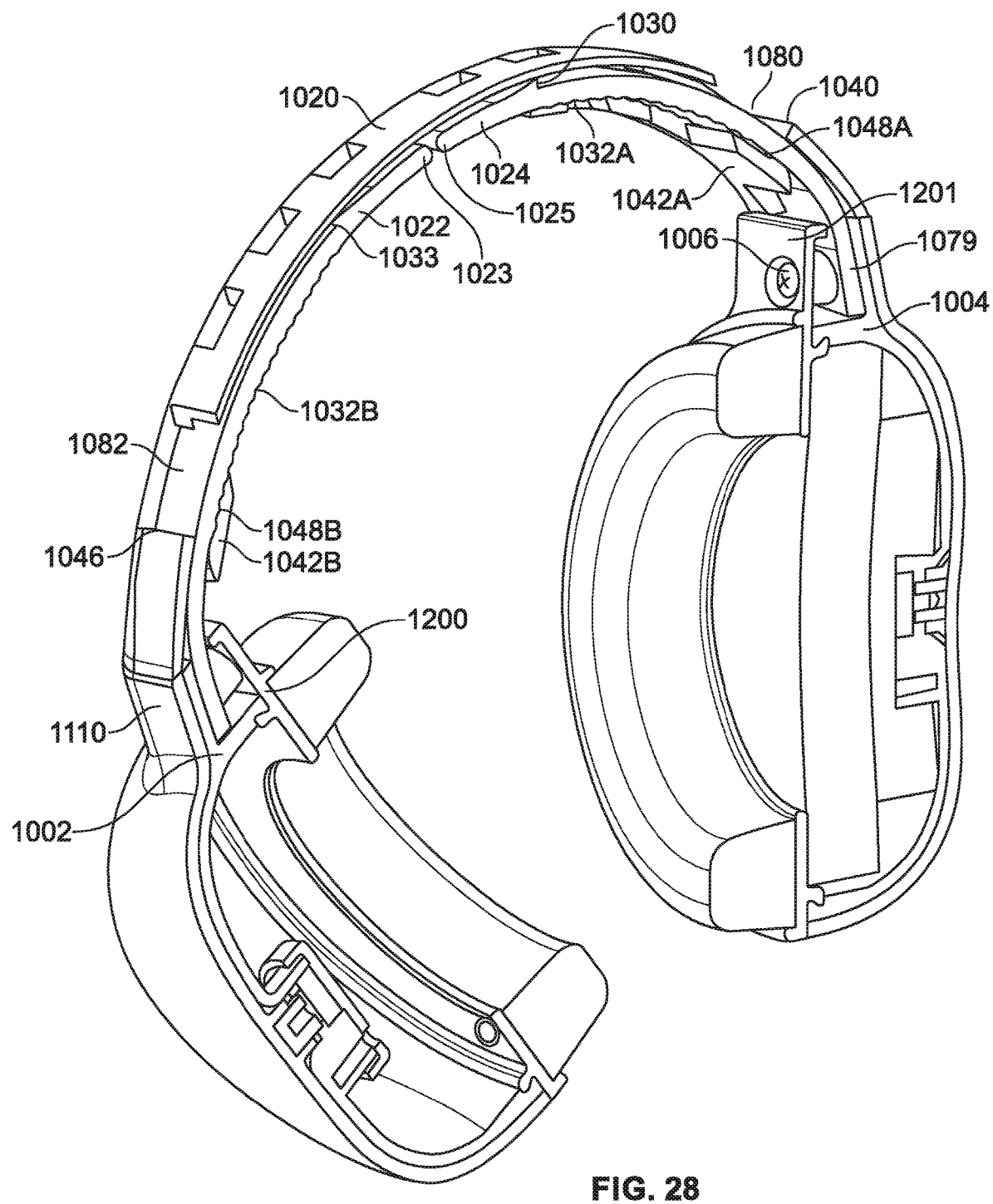
FIG. 28 shows the embodiment shown in FIG. 27 with portions removed.
Figure 30:
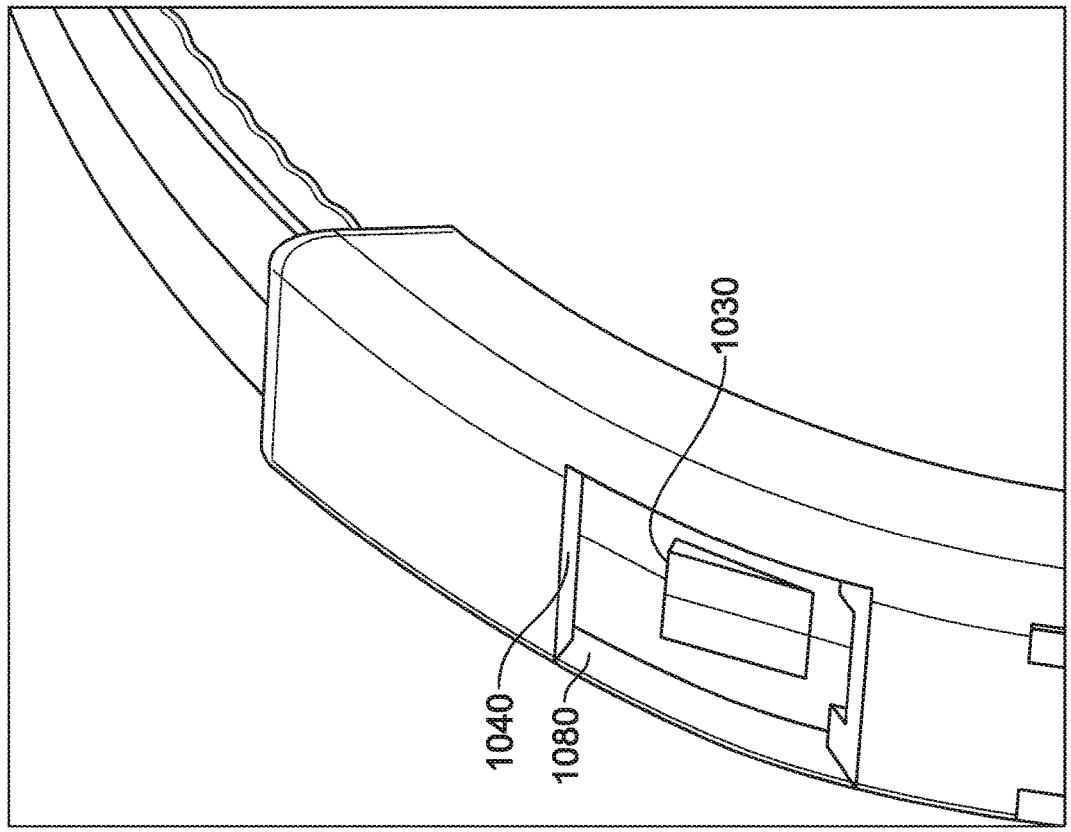
FIG. 30 is an exploded view of a headband section of the embodiment shown in FIG. 27.
Figure 29:
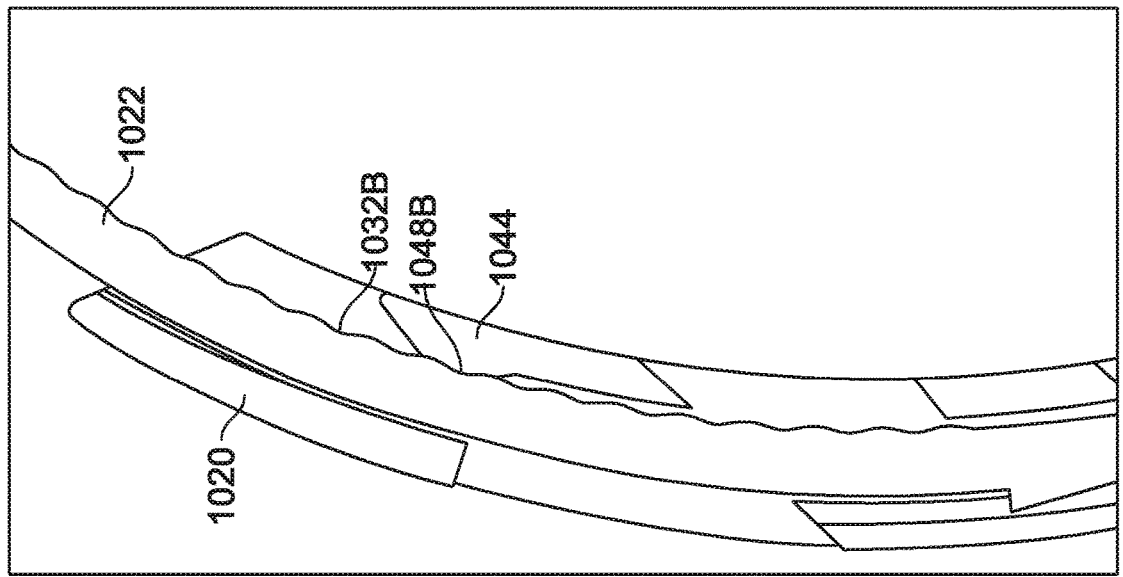
FIG. 29 is a partial cross-sectional view of a headband section of the embodiment shown in FIG. 27.

In a seventh embodiment, the present invention concerns an ear cover having telescoping headband and ear cups. This embodiment of the present invention provides, as shown in FIGS. 27-32, headband 1000 which holds ear cups 1002 and 1004. In a preferred embodiment, the ear cups are fastened to headband 1000 by the use of fasteners such as screw 1006. In a preferred embodiment, as shown in FIGS. 27-28, screw 1006 may go through ear pad frames 1200 and 1201, headband sections 1022 and 1024, ear cups 1002 and 1004 to anchor headband sections 1022 and 1024 into the channel formed by ear cup 1002 and 1004, and ear pad frames 1200 and 1201.

As shown in FIGS. 27-32, headband 1000 may be comprised of three pieces comprising of section 1020 which is adapted to slidingly engage and retain sections 1022 and 1024. Ends 1023 and 1025 of section 1022 and 1024 act as stops that designate the smallest setting of the device. For the long length stop, hooks 1030 and 1033 on sections 1022 and 1024 are provided. The hooks are adapted to catch edges 1040 and 1046 of section 1020 creating a hard stop that prevents sections 1022 and 1024 from pulling completely out of section 1020. Each hook can be initially installed by deflecting the housing then spring into an engagement when released by openings 1080 and 1082 in section 1020.

Headband 1000 may further include numerous stopping points on 1022 and 1024, exemplified by 1032A and 1032B and singular stopping points 1048A and 1048B located on headband 1020. As shown, bumps 1032A and 1032B are located on sections 1022 and 1024. Bumps 1048A and 1048B are located on portions 1042A and 1042B of section 1020. The bumps are configured to mate together. The bumps are arranged to have a consistent resistance.

In other aspects, as shown in FIG. 27, narrowed or tapered ends 1100 and 1110 are provided. Each end forms a channel that is U-shaped and configured to receive sections 1022 of 1024, respectively. By nesting sections 1022 and 1024 within the channel, the headband is not able to rock on the axis formed by the single fasteners that holds the headband in place such as screw 1006. In addition, the profile of the ends may match the profile of section 1020. For example, as shown in FIG. 27, distal end 1122 of end 1110 matches distal end 1123 of section 1022 to form a smooth continuous appearance when the distal ends are touching. This not only is aesthetically pleasing but it also forms a stop that keeps the outer shells in place with the unique shape at the top. The shell cannot be twisted off or easily taken off because of this and must be pulled outwardly and away from the ear cup to be removed.

Figure 31:
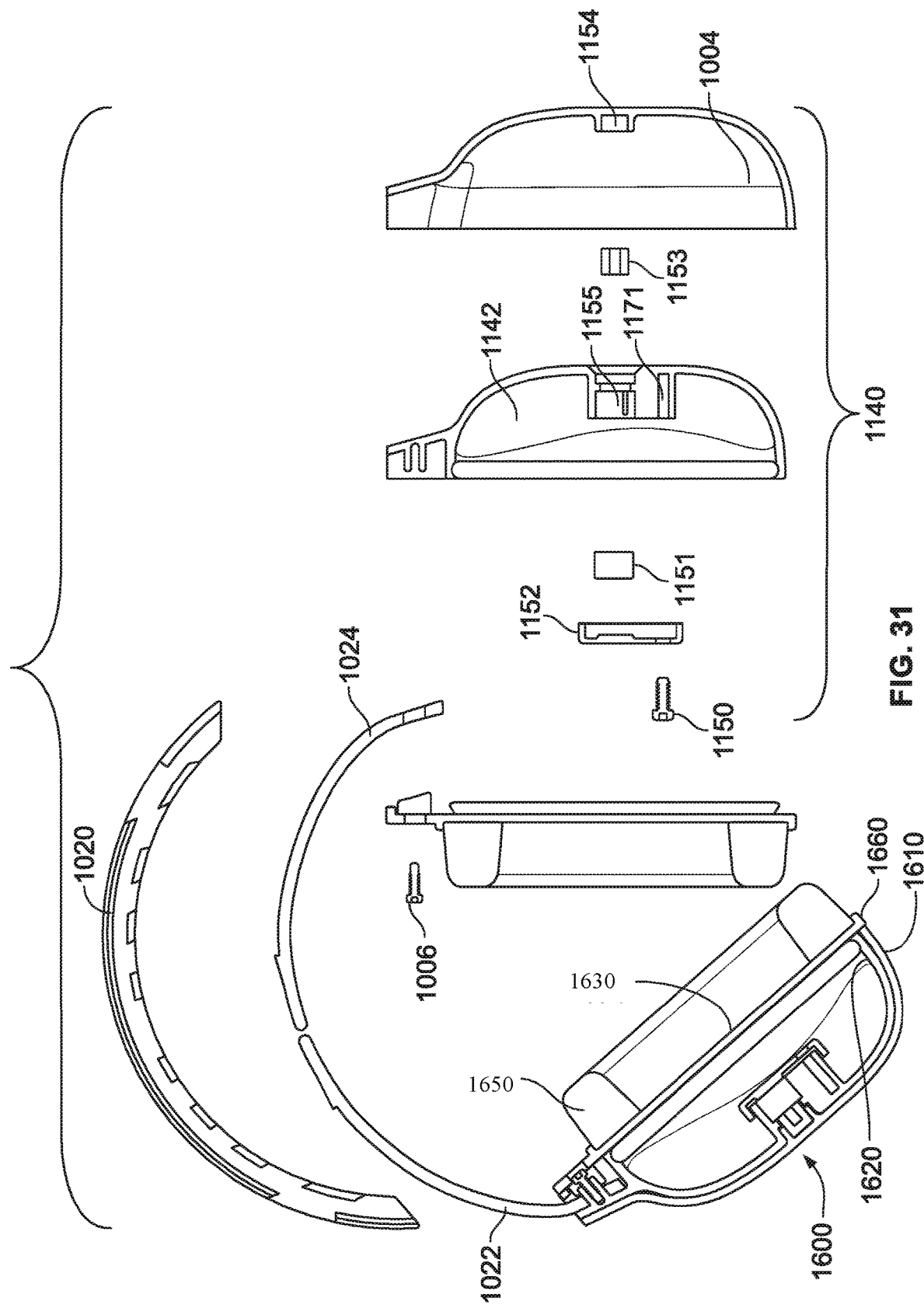
FIG. 31 is a schematic of the embodiment shown in FIG. 27.
Figure 32:
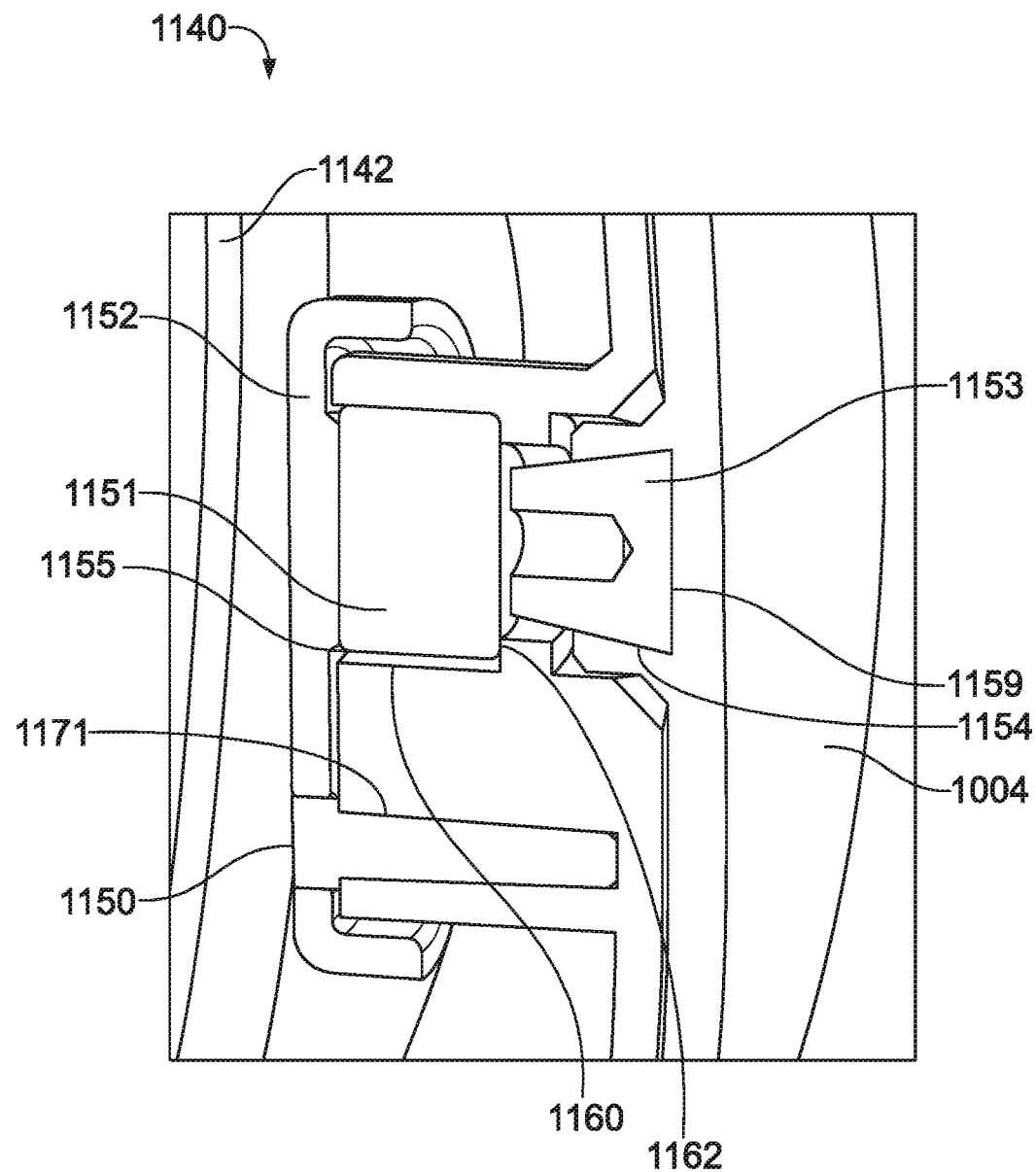
FIG. 32 is a partial cross-sectional view of a section of the embodiment shown in FIG. 27.

In another embodiment, the present invention concerns an ear cover that enhances the child safety of the product by deploying features that positively retain some of the small, ingestible parts of the device. As shown in FIGS. 31 and 32, this embodiment features ear cover assembly 1140 including fastener 1150, plate 1152, magnet 1151 which acts as a first magnetic material, ear cup 1142, opening or slot 1155, pin 1153 which acts as a second magnetic material, shell 1004, opening or slot 1171 and opening or slot 1154. The magnetic materials may be either two magnets that are attractive or a magnet and a material that is attracted to the magnet.

Magnet 1151 is secured within slot or opening 1155. In a preferred embodiment, as shown in FIG. 32, slot 1155 is defined by sidewall 1160 inside of inner ear cup 1142. Slot 1155 further includes an edge 1162 which may be in the form of an annular rim. Edge 1162, sidewall 1160 and plate 1152 function as stops that retain magnet 1151 from coming out or being pulled out of the device, which is important for safety.

As shown in FIGS. 31 and 32, this embodiment also includes steel pin 1153 secured in outer shell 1004 which is positioned to engage magnet 1151. Pin 1153 is secured within shell 1004 inside opening 1154 which is designed to prevent pin 1153 from sliding out of opening 1154. Locking pin 1153 within opening 1154 may be done by forming opening 1154 into to have a larger based-end 1159 and narrower end, which may be tapered, in the form of a truncated cone and in other configurations known to those of skill in the art. As shown, pin 1153 may have a shape that matches the shape of opening 1154 to nest therein.

As shown in FIGS. 31 and 32, fastener 1150 is inserted through plate 1152 and into bore 1171 in inner ear cup 1142. Fastener 1150 may be glued in place or held by threads. This binds the structure together.

In another embodiment, the present invention concerns an ear cover having a N52 Magnet with ¼" thickness, which optimizes the strength to secure the shell in place, while not requiring too much effort to remove. However, the force is strong enough to assist in preventing small children from removing the shell.

Figure 33:
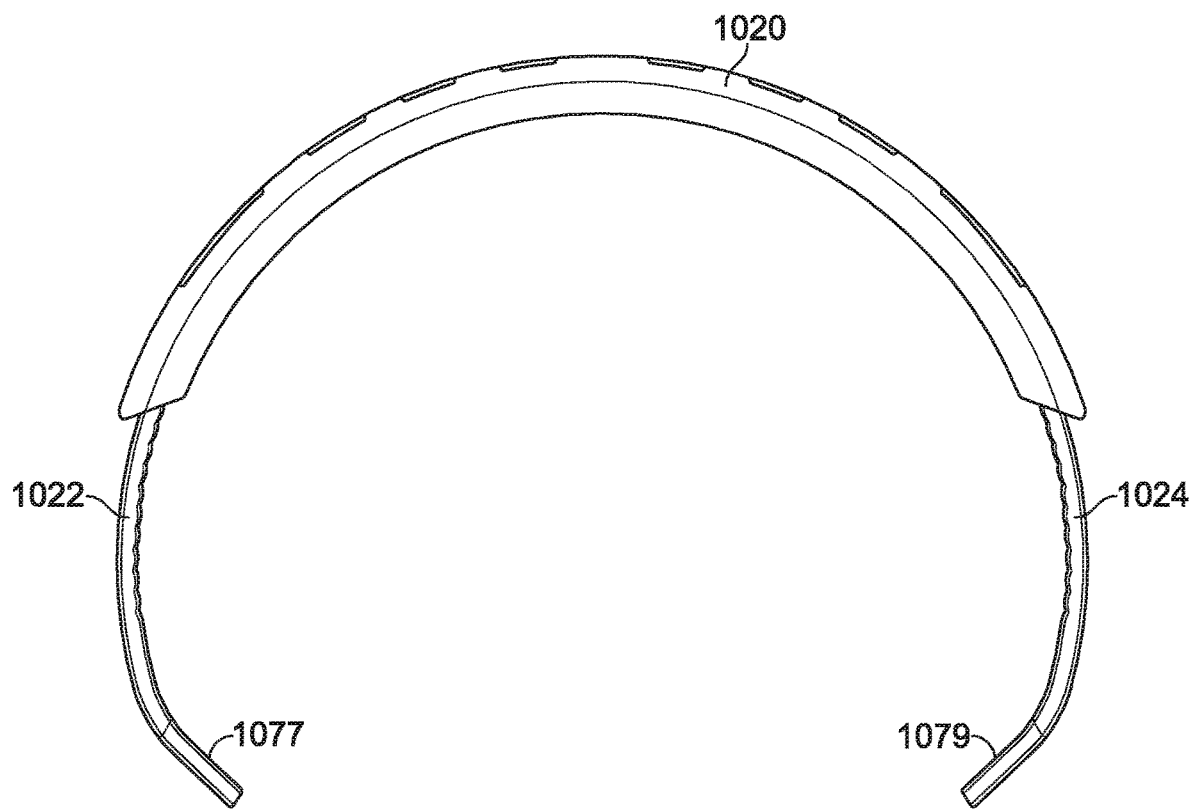
FIG. 33 illustrates a second headband that may be used with the embodiments of the present invention.

In other aspects, the present invention concerns earmuffs that optimize fit, seal, and attenuate noise as shown in FIG. 33. Headband 1020 and arms 1022 and 1024 have a uniform curve until the distal ends. Each distal end 1077 and 1079 is linear and slants or angles inward towards the users' ears, which allows the earmuff to rest on the side of the head more securely, which maximizes the seal for the best noise reduction possible.

Figure 34:
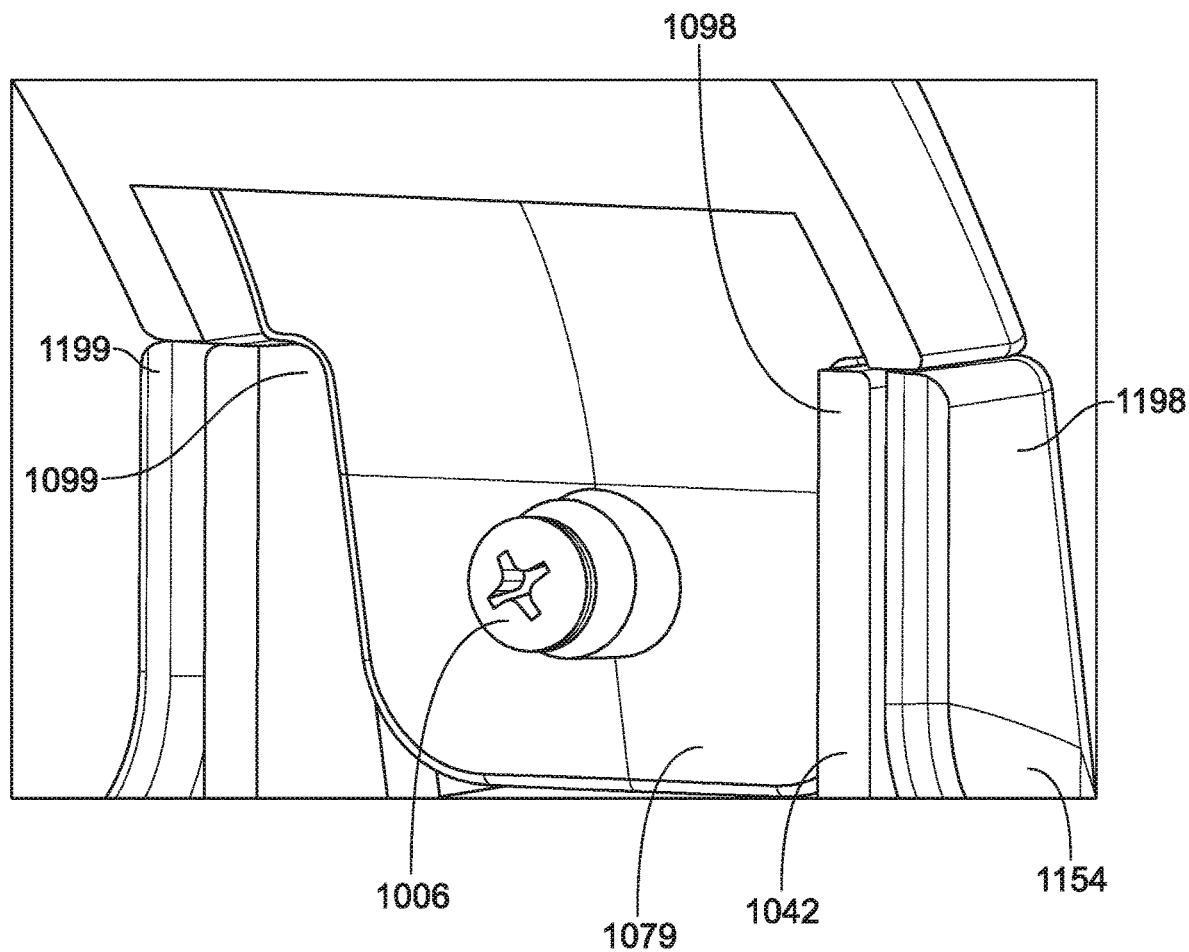
FIG. 34 is an exploded view showing how the headband shown in FIG. 33 may be used with the embodiments of the present invention.

As shown in FIG. 34, distal end 1079 is located in a channel defined by edges 1098 and 1099 of ear cup 1042 which may be connected to a third edge (not shown) to form a 3-sided channel. The channel may be configured to form a narrow end channel as described above. As also shown, the channel of ear cup 1042 is located in a channel defined by edges 1198 and 1199 of shell 1154 which may be connected to a third edge (not shown) to form a 3-sided channel. The channel may be configured to form a narrow end channel as described above. This arrangement forms a stop that prevents the rotational movement of the assembly.

As shown in FIGS. 27, 28 and 31, in other aspects, a portion of ear padding frame 1201 and ear cup 1004 snap-fit forming a channel that houses the tapered distal end of the headband.

In other aspects as shown in FIG. 31, assembly 1600 includes outer shell 1610, ear cup 1620, and frame 1630 having thereon pad 1650. As shown outer shell 1610 covers ear cup 1620. Frame 1630 is larger in size than ear cup 1620 and is sized to match shell 1610 to form a flush fit connection 1660. Flush-fit connection 1660 provides a seamless appearance between shell 1610 and frame 1630.

While the foregoing written description enables one of ordinary skill to make and use what is considered presently to be the best mode thereof, those of ordinary skill will understand and appreciate the existence of variations, combinations, and equivalents of the specific embodiment, method, and examples herein. The disclosure should therefore not be limited by the above-described embodiments, methods, and examples, but by all embodiments and methods within the scope and spirit of the disclosure.

What is claimed is:

1. An ear covering device comprising: an outer shell that is releasably detachable to an ear cup and said outer shell is comprised of mirror-image halves, said mirror-image halves snap-fit to each other to attach to an ear cup.

2. The device of claim 1 wherein said outer shell is releasably detachable to an ear cup by a magnetic connection.

3. The device of claim 1 wherein said outer shell includes a projection terminating in a material that forms a magnetic connection to an ear cup.

4. The device of claim 1 wherein said outer shell includes a projection terminating in a material that forms a magnetic connection to an ear cup.

5. The device of claim 1 wherein said outer shell is comprised of mirror-image halves, said mirror-image halves snap-fit to each other to form a channel that is attached to an ear cup.

6. An ear covering device comprising: an outer shell that is releasably detachable to an ear cup; said outer shell is comprised of mirror-image halves connected by a flexible channel, each of said mirror-image halves has an edge, said edges moveable between an open and closed position, when said mirror-image halves are in said open position, said spaced apart, and when said mirror-image halves are in said closed position, said shell is attached to an ear cup.

7. The device of claim 4 wherein said outer shell is releasably detachable to an ear cup by a magnetic connection.

8. An ear covering device comprising: a headband having opposing ends, at least one ear cup connected to one of said ends, and a shell releasably connectable to said ear cup; said outer shell is comprised of mirror-image halves connected by a flexible channel, each of said mirror-image halves has an edge, said edges are near one another when said mirror-image halves are in a closed position and spaced apart when said mirror-image halves are in an opened position, said shell attached to an ear cup when said mirror-image halves are in said closed position.

9. The device of claim 8 wherein said outer shell is releasably detachable to said ear cup by a magnetic connection.

10. The device of claim 8 wherein said outer shell includes a projection terminating in a material that forms a magnetic connection to said ear cup.

11. The device of claim 8 wherein said outer shell snap-fits to said ear cup.

12. The device of claim 8 wherein said outer shell is comprised of mirror-image halves, said mirror-image halves snap-fit to said ear cup.

13. The device of claim 8 wherein said outer shell includes a projection that snap-fits to said ear cup.

14. An ear covering device comprising: a headband having opposing ends, at least one ear cup connected to one of said ends, and a shell releasably connectable to said ear cup;
a first opening and a shell pin, said first opening shaped retains said shell pin in said opening;
said shell pin nests within said opening;
said ear cup includes a second opening terminating in an edge that is narrower than said second opening, and an ear cup retained in said second opening by said edge; and
a plate, fastener and a bore in the inner ear cup; said plate located opposite said edge and said fastener located in said bore; and said plate, said fastener holds said headband to said ear cup.

15. The device of claim 14 further including a headband comprised of a main housing and two movable arms therein; and a fastener that connects said ear cup to one of said moveable arms.

16. The device of claim 15 wherein said movable arms are curved and have linear distal ends that angle inwardly.

17. The device of claim 16 wherein said outer shell includes a channel, said ear cup includes a channel; said linear distal end of said moveable arm is located in said channel of said ear cup and said channel of said ear cup is located in said channel of said shell.

18. The device of claim 17 further including a frame having a pad thereon, a portion of said frame and said channel of said ear cup forms an opening in which said linear distal end of said moveable arm is secured.

19. The device of claim 17 wherein locating said channel of said ear cup located in said channel of said shell forms a stop that prevents said shell from being twisted off said ear cup.

20. The device of claim 17 wherein said ear cup pin and said shell pin magnetically connect to attach said shell to said ear cup.

21. The device of claim 20 wherein said channel of said ear cup is a 3-sided, tapered channel and said channel of said shell is a 3-sided, tapered channel.

22. The device of claim 21 wherein said ear cup includes an annular edge sized to receive said shell.

23. The device of claim 22 further including a frame having a pad; said outer shell sized to cover said ear cup; said frame is larger than said ear cup; and said frame is sized to match to said shell to form a flush fit connection between said frame and said shell.

24. The device of claim 14 wherein said first opening is shaped to taper inwardly from a base to a narrower end, said narrower end retains said shell pin in said first opening.

25. The device of claim 14 wherein said shell pin is tapered to nest within said first opening.

26. An ear covering device comprising: a headband having opposing ends, at least one ear cup connected to one of said ends, and an outer shell releasably connectable to said ear cup; said ear cup including a shell pin receiving opening; said outer shell including a shell pin; said shell pin receiving opening shaped to retain said shell pin in said shell pin receiving opening; said shell pin nests within said shell pin receiving opening; said headband comprised of a main housing and two movable arms therein; a fastener that connects said ear cup to one of said moveable arms; said movable arms are curved and have linear distal ends that angle inwardly; said outer shell includes a channel, said ear cup includes a channel; said linear distal end of said moveable arm is located in said channel of said ear cup and said channel of said ear cup is located in said channel of said shell; said ear cup includes an annular edge sized to receive said shell; and a frame having a pad; said outer shell sized to cover said ear cup; said frame connected to said ear cup and is larger than said ear cup; and said frame is sized to match to said shell to form a flush fit connection between said frame and said shell.

27. The device of claim 26 wherein said ear cup and said outer shell are magnetically connected.

\* \* \* \* \*